(12) United States Patent
Benning et al.

(10) Patent No.: US 7,951,342 B2
(45) Date of Patent: May 31, 2011

(54) STERILIZING APPARATUS

(75) Inventors: Gary W. Benning, Greenville, OH (US); Michael J. Coyle, Huber Heights, OH (US); Ronald A. Gatchell, Tipp City, OH (US); Richard L. Jones, Eaton, OH (US); Philip Marc Stewart, Greenville, OH (US)

(73) Assignee: Midmark Corporation, Versailles, OH (US)

( * ) Notice: Subject to any disclaimer, the term of this patent is extended or adjusted under 35 U.S.C. 154(b) by 144 days.

(21) Appl. No.: 10/556,479

(22) PCT Filed: Jun. 11, 2003

(86) PCT No.: PCT/US03/18474
§ 371 (c)(1),
(2), (4) Date: Nov. 14, 2005

(87) PCT Pub. No.: WO2005/004931
PCT Pub. Date: Jan. 20, 2005

(65) Prior Publication Data
US 2006/0251540 A1 Nov. 9, 2006

(51) Int. Cl.
*A61L 2/00* (2006.01)
*A61L 9/00* (2006.01)
*A61L 2/08* (2006.01)

(52) U.S. Cl. ........ 422/299; 422/292; 422/295; 422/297; 422/298; 422/26

(58) Field of Classification Search .................. 422/299, 422/295, 298, 26
See application file for complete search history.

(56) References Cited

U.S. PATENT DOCUMENTS
3,144,957 A * 8/1964 Anderson ..................... 220/316
(Continued)

FOREIGN PATENT DOCUMENTS
EP 0 290 929 A2 11/1988
(Continued)

OTHER PUBLICATIONS

European Patent Office, Supplementary European Search Report in European Application No. EP 03 81 7454 dated Dec. 15, 2008.

*Primary Examiner* — Sean Conley
*Assistant Examiner* — Regina Yoo
(74) *Attorney, Agent, or Firm* — Wood, Herron & Evans, LLP

(57) ABSTRACT

A sterilizer (20) is provided having a steam filled sterilizer chamber (24) for sterilizer articles placed within the chamber (24). An electronic air valve (186) is provided to control the venting rate of the steam is vented back to a water reservoir (140) after the articles have been sterilized. The electronic air valve (186) also vents the chamber (24) in a controlled manner during the heat up portion of the sterilization cycle to obtain an optimum saturated steam environment with the chamber (24) for the sterilizing process. The sterilizer (20) has pre-programmed and programmable sterilization cycles. And the drying times of each of these cycles is programmable by a user. The programmable sterilization cycles also provide a programmable vent rate which may be selected by the user to minimize damage to the sterilized articles. A steam condensing coil (200) is associated with the water reservoir (140) to minimize pressure build up within the water reservoir (140). The sterilizer (20) uses sensed pressure within the sterilizer chamber (24) to control heating of the chamber (24) to a predetermined sterilization temperature set point during a sterilization cycle. A motor (114) controls a door lock mechanism to open the door (32) of the sterilizer (20) following the sterilizing portion of the sterilization cycle.

7 Claims, 16 Drawing Sheets

U.S. PATENT DOCUMENTS

| | | | |
|---|---|---|---|
| 3,469,132 A * | 9/1969 | Haydon et al. | 310/163 |
| RE27,545 E * | 1/1973 | Guy | 219/412 |
| 3,859,979 A * | 1/1975 | Gilliom | 126/197 |
| 3,861,873 A | 1/1975 | MacFarlane et al. | 31/56 |
| 4,374,320 A * | 2/1983 | Barnett | 219/413 |
| 4,685,709 A * | 8/1987 | Kambic | 292/201 |
| 4,932,160 A | 6/1990 | Sperko | 49/254 |
| 5,223,229 A * | 6/1993 | Brucker | 422/116 |
| 5,277,875 A | 1/1994 | Albright et al. | 422/109 |
| 5,730,944 A | 3/1998 | Peake | 422/111 |
| 6,058,247 A | 5/2000 | Lahey et al. | 392/399 |
| 6,069,466 A * | 5/2000 | Noritake et al. | 318/685 |
| 6,488,675 B1 * | 12/2002 | Radford et al. | 604/540 |
| 2002/0085945 A1 | 7/2002 | Florkey et al. | |

FOREIGN PATENT DOCUMENTS

| | | |
|---|---|---|
| EP | 0 477 561 A2 | 4/1992 |
| WO | 92-01479 A1 | 2/1992 |

* cited by examiner

STERILIZING APPARATUS

FIELD OF THE INVENTION

The present invention relates generally to sterilizers and, more particularly, to a sterilizer for sterilizing articles under the influence of heat and pressure within a sterilizing chamber.

BACKGROUND OF THE INVENTION

Sterilizers are widely used to sterilize articles in medical and dental offices, hospitals, clinics, nursing homes, laboratories and other facilities to sterilize heat and moisture stable reusable articles, including dental handpieces. Sterilizers typically employ a steam filled sterilizer chamber for containing the article to be sterilized and a heater located within the chamber for increasing the temperature and pressure inside the chamber to a point where the article is sterilized. Sterilizers have a door which is mounted to open and close relative to an opening of the sterilizer chamber so that the articles may be placed within the chamber to be sterilized and thereafter removed.

In a typical sterilization cycle for solid articles, the articles are sealed within the chamber of the sterilizer and steam is supplied to the chamber. The steam may either be provided from a separate steam producing chamber or by supplying water to the chamber and heating the chamber until the water evaporates. In either case, the chamber is provided with a heater to elevate the temperature in the chamber and cause an accompanying increase in pressure such that sterilization of the articles is effected. Further, the presence of steam in the chamber facilitates an increase in pressure therein whereby the temperature and time required for completing the sterilization process may be kept to a minimum.

Sterilizers have conduits for conveying water from the water reservoir to the sterilizer chamber at the beginning of the sterilization cycle and for venting steam from the chamber back to the reservoir after the articles have been sterilized. The returned steam from the chamber is condensed in the water reservoir for reuse in a subsequent cycle. Valves are fluidly connected to the conduits and are controlled so that the proper sequence of filling the chamber with water and venting the steam from the chamber back to the reservoir occurs during the sterilization cycle. Following the sterilizing and venting portions of the sterilization cycle, the door may be opened while additional heat is provided within the sterilizer chamber to dry the sterilized items during a drying portion of the cycle.

Typically, sterilizers have pre-programmed sterilization cycles which are selected by a user for the particular article to be sterilized. Each pre-programmed sterilization cycle has a set sterilization temperature set point, sterilization time, and drying time for the cycle. However, certain situations may occur where the parameters of the pre-programmed sterilization cycles do meet the particular sterilization requirements of a user. Either the articles do not get adequately sterilized due to insufficient sterilization temperature or sterilization time or the articles are still damp after the sterilization cycle due to insufficient drying time.

During the sterilization cycle, it is desirable to obtain an optimum saturated environment of steam within the sterilizing chamber. Oftentimes, however, as the water within the chamber is heated and evaporated into steam, there is residual air within the chamber that prevents this optimum saturated steam environment from being obtained.

Also, it is desirable to maintain the temperature within the chamber very close to the sterilization temperature set point to assure that the articles are properly sterilized during the sterilization cycle. However, the temperature within the chamber is oftentimes difficult to accurately control and temperature sensors have not provided the degree of temperature sensing accuracy that may be desired to monitor and control the chamber temperature during the sterilization cycle.

During the venting process, the steam is vented back to the water reservoir at a fixed vent rent to reduce the pressure within the sterilizer. Under certain circumstances, the venting of the steam, and the associated drop in pressure within the sterilizer chamber, is too rapid for certain articles being sterilized and the articles become damaged or are otherwise detrimentally affected by the rapid drop in pressure within the chamber following sterilization.

Venting of the steam from the sterilizing chamber to the water reservoir oftentimes causes problems since the water reservoir may be unsealed to prevent a build up of pressure within the water reservoir resulting from the returned steam. A build up of pressure within the water reservoir, if not properly vented, may cause the water within the reservoir to be expelled from a filling portion of the reservoir. When the reservoir has an opening to vent the returned steam, the steam is vented within the housing of the sterilizer which increases moisture within the sterilizer. This may cause problems to mechanical and electrical components within the housing which may be sensitive to the increased levels of moisture over time.

Oftentimes, the door is opened when there is some residual pressure remaining in the chamber after the sterilization process, and opening of the door can create a noise at times which may startle those located near the sterilizer or may otherwise be a nuisance in certain environments.

Therefore, there is a need for a sterilizer which overcomes these and other shortcomings and drawbacks of sterilizers heretofore know.

SUMMARY OF THE INVENTION

The present invention overcomes the foregoing and other shortcomings and drawbacks of sterilizers heretofore known. While the invention will be described in connection with certain embodiments, it will be understood that the invention is not limited to these embodiments. On the contrary, the invention includes all alternatives, modifications and equivalents as may be included within the spirit and scope of the present invention.

The present invention provides a sterilizer for sterilizing articles in a steam environment at above atmospheric pressures and at predetermined sterilization temperatures. The sterilizer of the present invention includes a sterilizing chamber having a chamber opening at a front portion of the chamber through which articles may be placed into the chamber. A water reservoir is provided to partially fill the chamber with water prior to a sterilization cycle. A heating element is located within the chamber and is operable to heat and evaporate the water into steam to heat and pressurize the chamber during a sterilization cycle and thereby sterilize the articles received within the chamber. The sterilizer has conduits for conveying water from the water reservoir to the sterilizer chamber at the beginning of the sterilization cycle and for venting steam from the chamber back to the reservoir after the articles have been sterilized. The returned steam from the chamber is condensed in the water reservoir for reuse in a subsequent cycle. Valves are fluidly connected to the conduits and are controlled so that the proper sequence of filling the chamber with water and venting the steam from the chamber back to the reservoir occurs during the sterilization cycle.

A door is mounted adjacent to the front portion of the chamber and is movable from a closed position in engagement with the chamber to close off the chamber opening and an open position spaced from the chamber for insertion of articles into the chamber. The door is held in position adjacent to the chamber opening by a door lock mechanism. In accordance with one aspect of the present invention, a motor is provided to actuate the door lock mechanism so that the door opens quietly following the sterilizing portion of the sterilization cycle. In one embodiment of the present invention, the motor comprises an AC synchronous motor which is operatively connected to the door lock mechanism and is operable to actuate the door lock mechanism to open the door while additional heat is provided within the sterilizer chamber to dry the sterilized articles during a drying portion of the cycle.

The water reservoir includes a baffle which separates the reservoir into front and rear portions wherein the front portion defines a water filling chamber of the reservoir and the rear portion forms a condensing chamber for receiving and condensing steam vented from the chamber. When the reservoir is filled with water to a level at or above a lowermost portion of the baffle, the baffle and the water together form a vapor barrier such that any steam located in the condensing chamber will be prevented from flowing into the filling chamber and out of a fill spout located on the front portion of the reservoir.

In accordance with another aspect of the present invention, a steam condensing coil, made of copper in one embodiment, is provided to fluidly connect air spaces of the condensing chamber and the filling chamber to effectively equalize the air pressures within the respective chambers and to condense steam within the coil as the steam travels from the condensing chamber to the filling chamber during a sterilization cycle. Air vapors within the steam condensation coil are directed to the filling chamber where the air vapors may be vented to atmosphere through the fill spout which is located outside of the sterilizer enclosure. The steam condensing coil is supported in such a way that any condensed steam within the coil will travel to the condensing chamber.

The sterilizer of the present invention provides four (4) pre-programmed sterilization cycles and two (2) user programmable sterilization cycles. The pre-programmed cycles include an "Unwrapped Cycle" for processing unwrapped articles, a "Pouches" cycle for processing articles sealed within a wrapped package, a "Packs" cycle for processing articles which are grouped in a pack such as a tray containing the articles wrapped in a sealed manner by a cloth covering, for example, and a "Dental Handpiece" cycle for processing dental instruments.

For each of the four pre-programmed cycles, the dry cycle duration of the sterilization cycle is preprogrammed. However, in accordance with another aspect of the present invention, the dry cycle duration for each of the four (4) preprogrammed cycles and two (2) programmable cycles is programmable by the user to define a user selected dry cycle duration in the range of 0-60 minutes in one embodiment of the present invention.

In accordance with still yet another aspect of the present invention, the sterilizer has user selectable vent rates for each of the user programmable sterilization cycles which define the rate at which the sterilizer vents the steam from the chamber back to the water reservoir following the sterilize portion of the sterilization cycle. One selectable vent rate, referred to as a "Fast Vent", causes a valve to open and remain open while the steam from the chamber is vented to the condensation chamber of the water reservoir. The other selectable vent rate, referred to as a "Slow Vent", causes the valve to open for one (1) second and close for fifty-nine (59) seconds during every minute of vent time according to one embodiment of the present invention. The "Slow Vent" vent rate may be desirable when there is a need to hold the pressure within the chamber and to gradually reduce the pressure so as to avoid a detrimental effect to the articles placed within the chamber.

In accordance with another aspect of the present invention, an electronic air valve is provided in fluid communication with water reservoir and the sterilizer chamber to vent steam from the chamber back to the reservoir. In one embodiment of the present invention, the electronic air valve is opened and closed multiple times, i.e., three (3) times, as the sensed steam temperature rises toward the sterilization temperature set point during the heat up portion of the sterilization cycle. The electronic air valve vents a mixture of air and steam from the chamber to the water reservoir multiple times during the heat up portion of the sterilization cycle so that residual air within the chamber is vented to obtain an optimum saturated environment of steam within the chamber during the sterilization cycle.

In accordance with yet another aspect of the present invention, the sterilizer of the present invention utilizes chamber pressure to control heating of the chamber to the sterilization temperature set point. The sterilizer samples the chamber pressure at various sensed chamber temperatures, and uses those pressure values, rather than sensed temperature values, to control heating of the chamber. In this way, the chamber temperature is accurately maintained very close to the sterilization temperature set point so that the chamber properly sterilizes the articles placed within the chamber.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE PREFERRED EMBODIMENT

Figure 1:
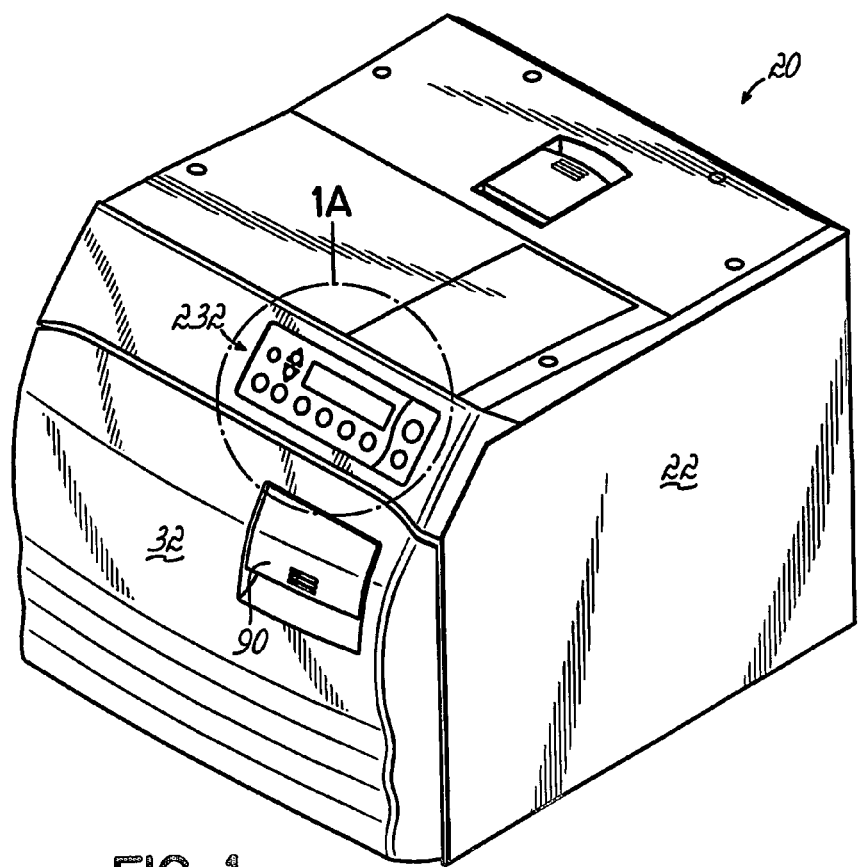
FIG. 1 is a perspective view of the outer housing of a sterilizer in accordance with the principles of the present invention.

Referring to Figures, and to FIGS. 1-4 in particular, a sterilizer 20 in accordance with the principles of the present invention includes an outer housing 22 within which a sterilizer chamber 24 is enclosed. The sterilizer chamber 24 includes an opening 26 (FIG. 2) at a front portion of the sterilizer 20 which is configured to receive articles (not shown) to be placed inside the sterilizer chamber 24. As may be seen in FIG. 2, the sterilizer chamber 24 is provided with support rails 28 for supporting article trays 30 within the chamber 24.

A door 32 defines a front portion of the sterilizer housing 22 and includes a chamber sealing plate 34 and an annular chamber seal 36 supported by the sealing plate 34. The sealing plate 22 is supported by upper and lower horizontal support bars 38, 40 which are mounted to respective horizontal supports 42, 44 by pivot pins 46, 48. Thus, the door 32 may be pivoted about a vertical axis toward and away from the chamber 24 whereby the seal 36 may contact a sealing surface 50 surrounding the chamber opening 26 to close and form an airtight seal around the opening 26, such that pressurized steam within the chamber 24 will be retained.

The upper and lower support bars 38, 40 carry a pair of locking pins 52, 54 (FIGS. 5A and 5B) at an end opposite from the pivot pins 46, 48 which cooperate with a pair of horizontal bars 56, 58 mounted in stationary relationship to the chamber 24. As may be best seen in FIGS. 2, 5A and 5B, the pair of locking pins 52, 54 extend through the upper and lower support bars 38, 40 to engage the pair of horizontal bars 56, 58.

Each of the pair of horizontal bars 56, 58 includes a horizontal upper surface 60 (FIGS. 5A and 5B) and apertures 62, 64 extending through the bars 56, 58, respectively, to form a first stop for the pins 52, 54 when the door 32 is in its closed position. The horizontal bars 56, 58 are further each provided with an elongated slot 66, 68 extending forwardly from the apertures 62, 64. A forward surface of each of the apertures 62, 64 adjacent to the slots 66, 68 form first stop surfaces 70, 72 for engaging a forwardly facing portion of each of the pins 52, 54 to prevent the door 32 from moving away from the chamber 24.

Each of the slots 66, 68 is defined by a horizontal pin supporting surface 74, 76 which is spaced vertically downwardly from the horizontal upper surface 60 of the bars 56, 58, and a vertical second stop surface 78, 80 extending between the horizontal upper surface 60 of the bars 56, 58 and the pin support surfaces 74, 76. The second stop surfaces 78, 80 face rearwardly toward the apertures 62, 64 to engage the pins 52, 54 after they are disengaged from the first stop surfaces 70, 72, as shown in FIG. 5B, to thereby hold the door 32 in a partially open position spaced from the opening 26 of the chamber 24. In one embodiment of the invention, the first and second stop surfaces 70, 72 and 78, 80, respectively, are spaced from each other a distance which will limit the movement of the door 32 to less than one inch from the closed to the partially open position, and preferably a distance of approximately one-half inch.

Figure 2:
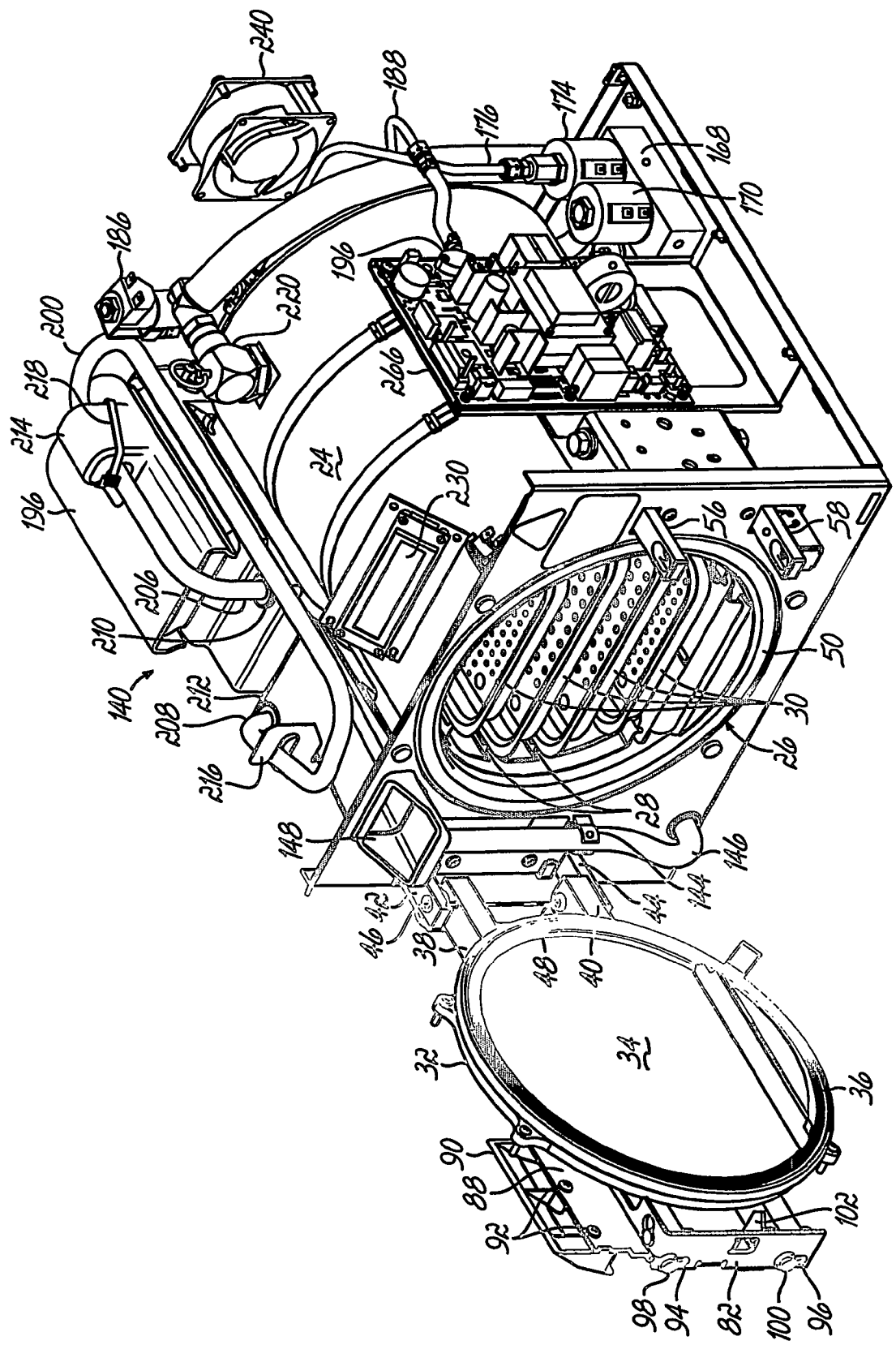
FIG. 2 is a perspective view of the sterilizer of the present invention with the housing removed and sterilizer door in a fully open position.
Figure 5A:
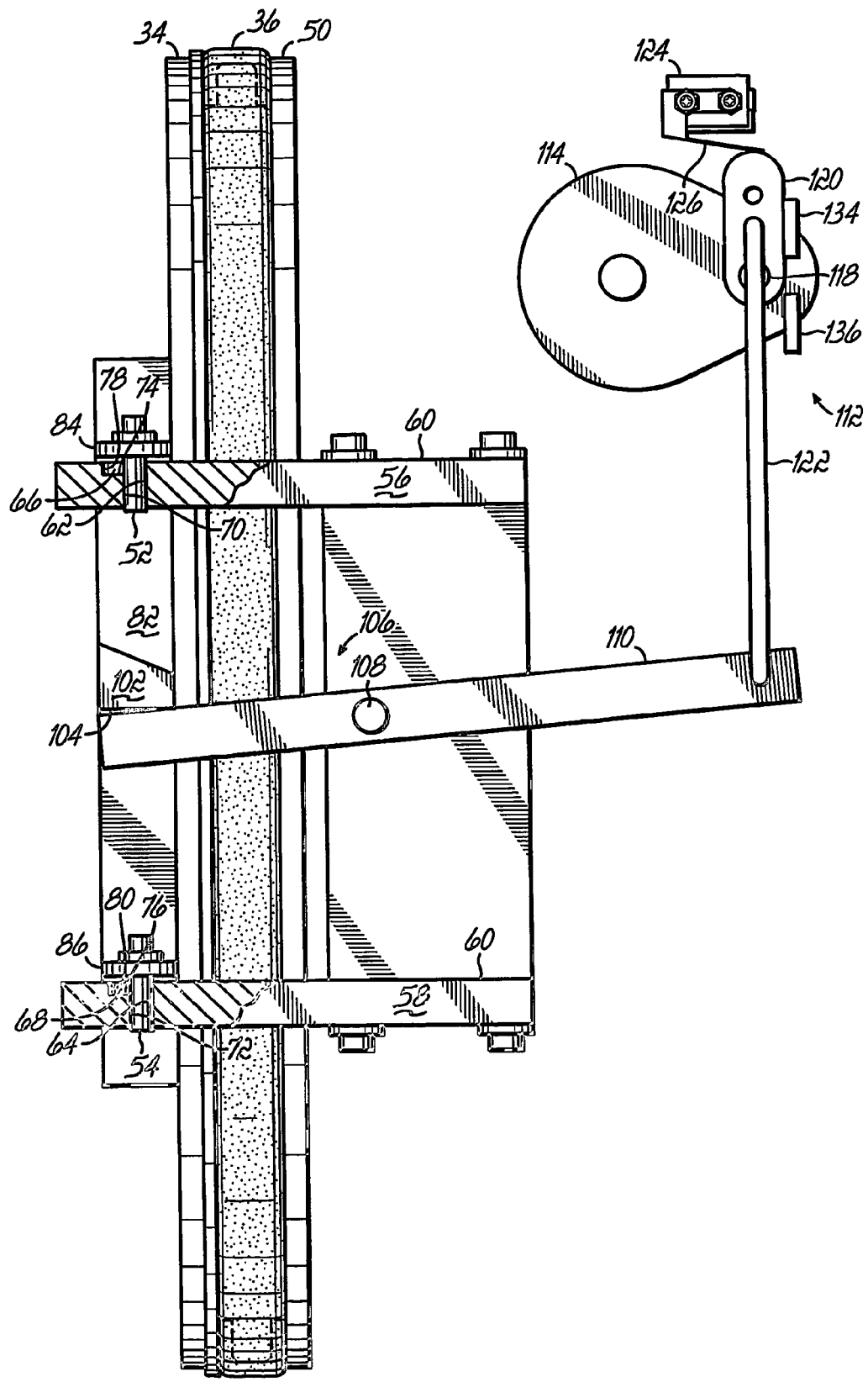
FIG. 5A is a diagrammatic side view of a door locking mechanism for the sterilizer door wherein the door is held in a fully closed position.
Figure 5B:
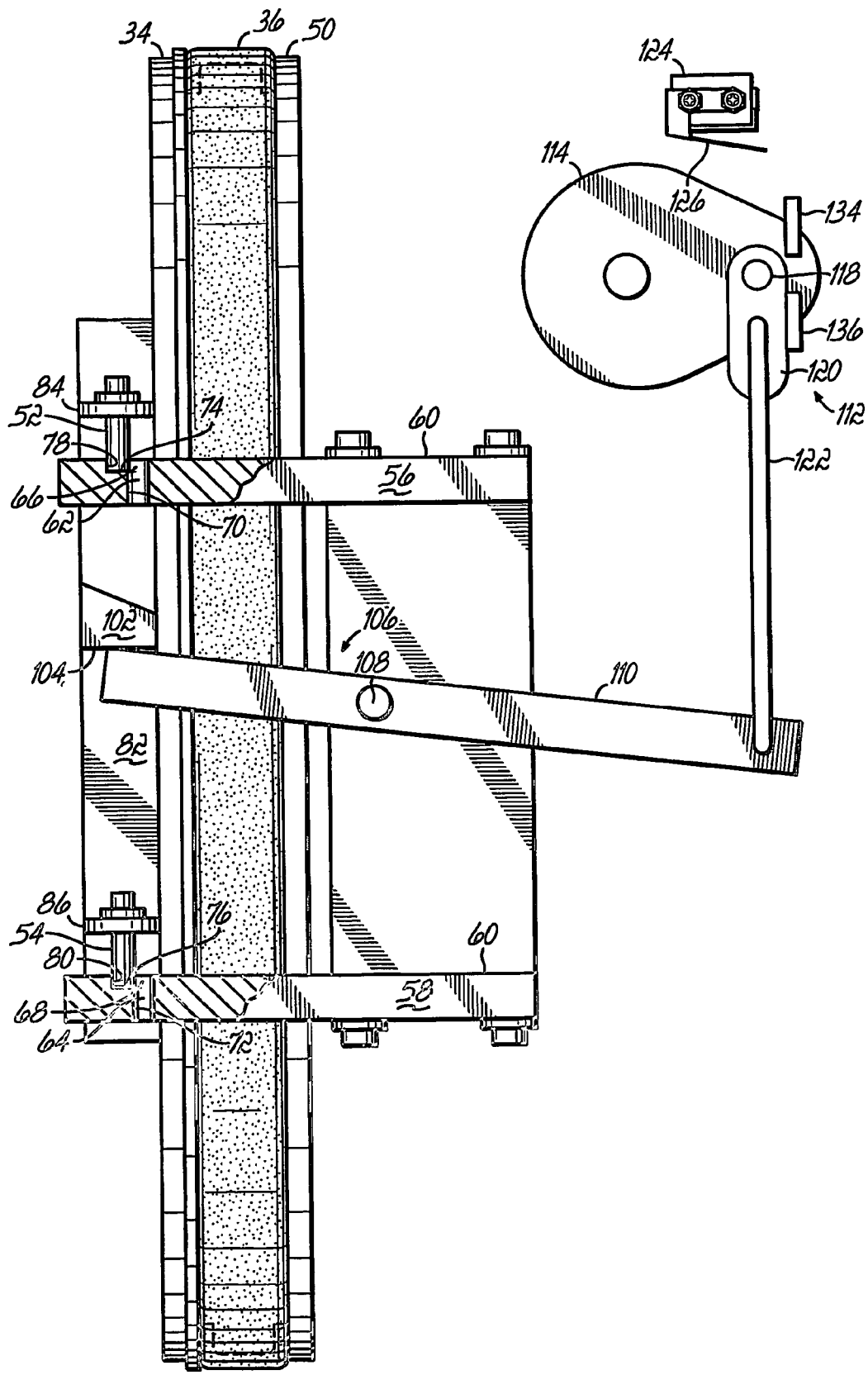
FIG. 5B is a view similar to FIG. 5A of the door locking mechanism for the sterilizer door wherein the door is held in a partially open position.

Further referring to FIGS. 2, 5A and 5B, a connecting member 82 extends vertically between the pins 52, 54 and pin carrier plates 84, 86 (FIGS. 5A and 5B) which connect the pins 52, 54 to the connecting member 82. The pin carrier plate 84 further includes a vertically extending handle attachment plate 88 (FIG. 2) which is attached to a handle 90 by appropriate fasteners 92.

As shown in FIG. 2, the connecting member 82 is formed with a pair of vertically extending slots 94, 96 and a pair of bolts 98, 100 pass through the slots 94, 96 to engage the upper and lower horizontal support bars 38, 40, respectively, whereby the connecting member 82 is guided for vertical movement relative to the door 32. Thus, by lifting the handle 90 upwardly, the locking pins 52, 54 will be guided in vertical movement by the slots 94, 96 and bolts 98, 100 such that the pins 52, 54 will be moved vertically in an upward direction whereby they may be disengaged from the apertures 62, 64 formed in the pair of horizontal bars 56, 58. In addition, a latch bracket 102 (FIGS. 2, 5A and 5B) is mounted to the connecting member 82 intermediate the horizontal support bars 38, 40 and includes a downwardly facing horizontal surface 104.

Figure 3:
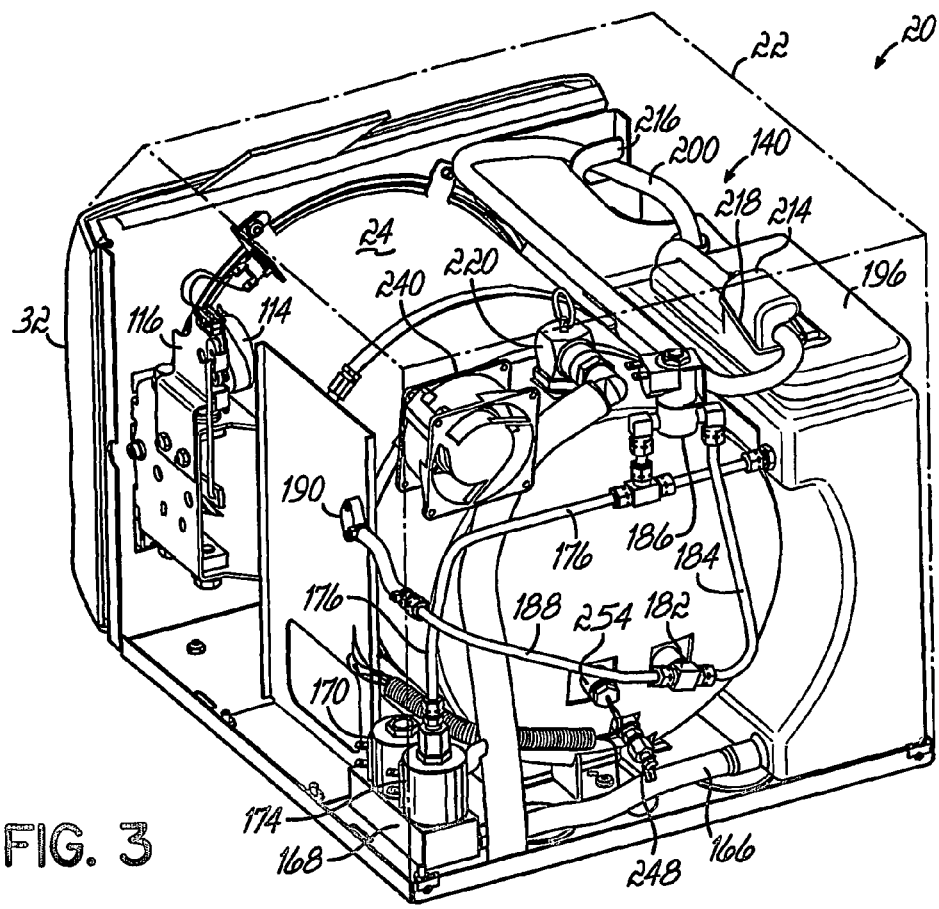
FIG. 3 is a perspective view illustrating the rear interior of the sterilizer.
Figure 4:
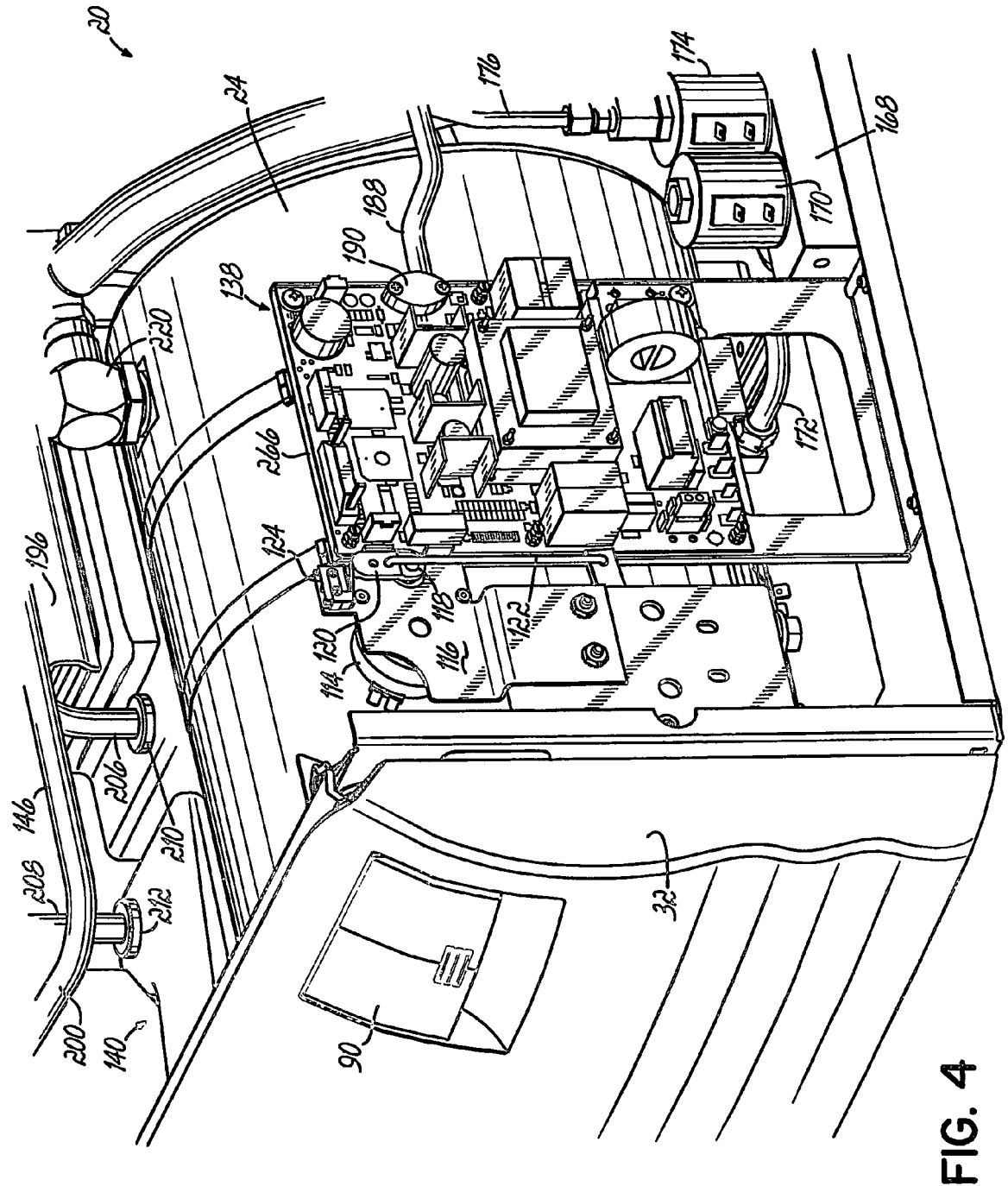
FIG. 4 is a partial perspective view illustrating a side interior of the sterilizer.

As shown in FIGS. 5A and 5B, a release bar 106 is mounted by a pivot pin 108 between the bars 56, 58 and extends in substantially a front to rear direction. A forwardly located upper surface of the release bar 106 engages the horizontal surface 104 of the latch bracket 102 when the door 32 is in its closed position. In accordance with one aspect of the present invention, a rearwardly located leg 110 of the release bar 106 is attached to a linkage assembly 112 which is actuated by an AC synchronous motor 114 (FIGS. 3, 4, 5A and 5B) mounted in stationary relationship to the bars 56, 58 on a support bracket 116 (FIGS. 3 and 4). The motor 114 has a rotatable motor shaft 118 connected to a cam member 120 which is mounted to rotate with the motor shaft 118. A generally outward portion of the cam member 120 is connected to the rear leg 110 of the release bar 106 through a connecting rod 122, whereby the rear leg 110 of the release bar 106 may be moved downwardly to pivot the forward portion of the release bar 106 in contact with the latch bracket 102 to move the latch bracket 102 upwardly. As will be described in greater detail below, the motor 114 may be actuated to cause the locking pins 52, 54 to move upwardly such that the pins 52, 54 are disengaged from the first stop surfaces 70, 72 and the door 32 is allowed to pivot outwardly until the pins 52, 54 contact the second stop surfaces 78, 80. Of course, other types of motors that will provide a continuous movement of the linkage assembly 112 are possible as well.

Referring to FIGS. 4, 5A and 5B, a switch 124 is mounted to the support bracket 116 and includes an actuation finger 126 extending downwardly therefrom. An outward portion of the cam member 120 is rotated in contact with the finger 126 when the door 32 is in its closed position to cause normally closed (NC) contacts 128 (FIG. 6) within the switch 124 to open. When a door opening operation is initiated during a sterilization cycle as will be described in greater detail below, the motor 114 is energized through a door relay 130 (FIG. 6) which has its normally open (NO) contacts 132 closed for fifteen (15) seconds. With the door relay 130 closed, the motor 114 is energized to rotate the cam member 120 in a counterclockwise direction away from vertical stop member 134 (FIGS. 5A and 5B) which, in turn, causes the rear leg 110 of the release bar 106 to move downwardly and thereby pivot the forward portion of the bar 106 in contact with the latch bracket 102 to move the latch bracket 102 upwardly. In this way, the locking pins 52, 54 are moved upwardly such that the pins 52, 54 are disengaged from the first stop surfaces 70, 72 and the door 32 is allowed to pivot outwardly until the pins 52, 54 contact the second stop surfaces 78, 80 as shown in FIG. 5B.

Figure 6:
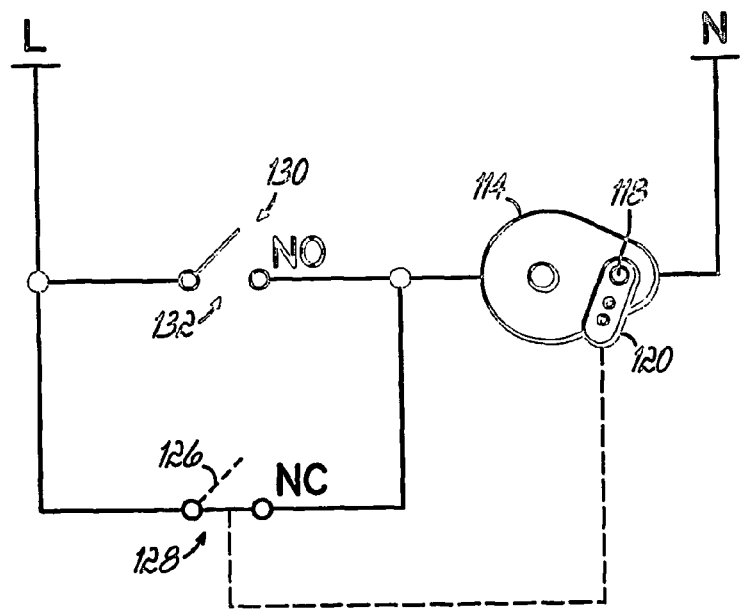
FIG. 6 is a schematic view of an electrical circuit used in the sterilizer to operate the door locking mechanism of FIGS. 5A and 5B.

Referring to FIGS. 5B and 6, when the cam member 120 is rotated in the counterclockwise direction to be free from contact with the actuation finger 126 of the switch 124, the normally closed (NC) contacts 128 (FIG. 6) within the switch 124 close to energize the motor 114 when the door relay 130 opens after the fifteen (15) second duration. The cam member 120 rotates in the counterclockwise rotation until it strikes a second vertical stop member 136 (FIGS. 5A and 5B) at which point the motor 114 automatically reverses itself and now rotates the cam member 120 back to its rest position as shown in FIG. 5A. In Its rest position, the cam member 120 again contacts the actuation finger 126 of the switch 124 to cause the normally closed (NC) contacts 128 (FIG. 6) within the switch 124 to open and thereby de-energize the motor 114. The switch 124 and door relay 130 are electrically coupled to a control 138 (FIGS. 4 and 11) which controls the operation of the sterilizer 20 as will be described further below.

Referring now to FIGS. 2, 7-10 and 17, a water reservoir 140 is located adjacent to the chamber 24 and extends in a front to rear direction along one side of the sterilizer 20. A front wall 142 (FIG. 17) of the water reservoir 140 is located adjacent to the opening 26 of the chamber 24 and includes a pair of clips 144 (one shown in FIG. 2) for mounting a flexible transparent tube 146 having an upper end which is open to the atmosphere and a lower end which opens into the bottom of the reservoir 140. Thus, the tube 146 forms a window through which the water level in the reservoir 140 may be viewed. Further, the tube 146 may be disengaged from the clips 144 and pivoted downwardly about its lower end to facilitate draining of water from the reservoir 140. A fill spout 148 is also located on the front wall 142 adjacent to an upper wall 150 (FIG. 17) of the reservoir 140 for filling the reservoir 140. The tube 146 and fill spout 148 are positioned such that they are covered by a portion of the door 32 when the door 32 is closed.

The reservoir 140 includes a baffle 152 (FIG. 17) which separates the reservoir into front and rear portions wherein the front portion defines a water filling chamber 154 of the reservoir 140 and the rear portion forms a condensing chamber 156 for receiving and condensing steam vented from the chamber 24. The baffle 152 extends from an uppermost portion of the reservoir at the upper wall 150 downwardly to a point below a predetermined minimum level for water in the reservoir 140.

When the reservoir 140 is filled with water to a level at or above a lowermost portion of the baffle 152, the baffle 152 and the water together form a vapor barrier such that any steam located in the condensing chamber 156 will be prevented from flowing into the filling chamber 154 and out of the fill spout 148 and thus water in the sterilizer system is efficiently recovered.

A condensing coil 158 (FIG. 17) is positioned within the condensing chamber 156 and lies substantially below the level of the water within the water reservoir 140. An inlet end 160 of the coil 158 is located adjacent to the upper wall 150 of the reservoir 140 and an exit end 162 of the coil 158 is located at a point above the level of the water such that the steam within the coil 158 travels upwardly as it is condensed and is discharged through the exit end at a point above the water level of the reservoir 140.

Figure 7:
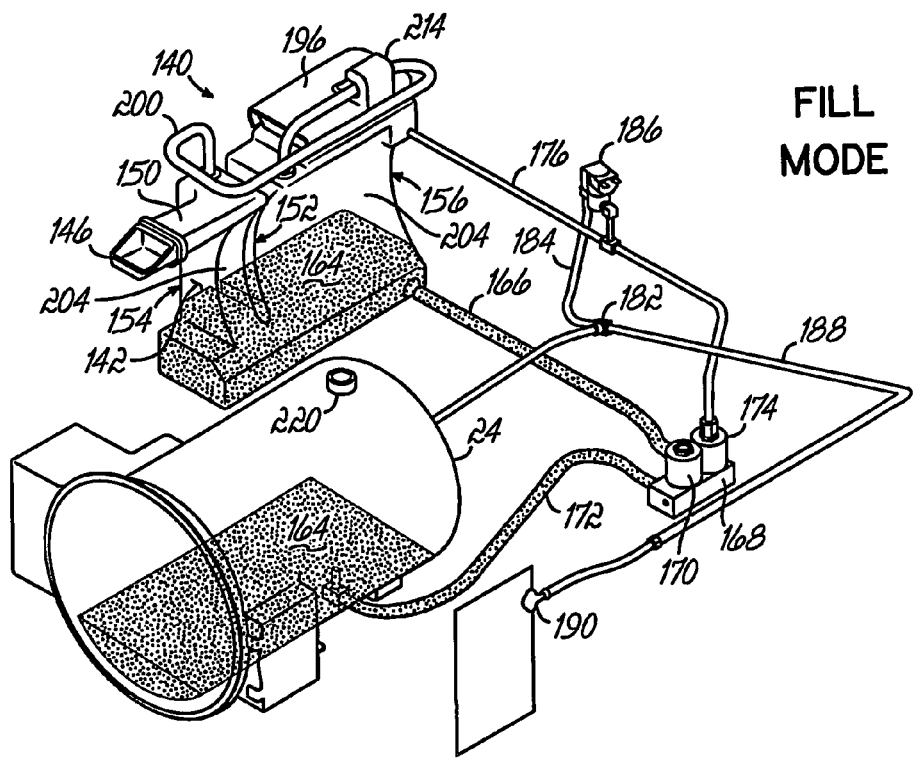
FIGS. 7-10 are diagrammatic views of the components of the sterilizer, illustrating steps which occur during a sterilization cycle.

Water, identified by numeral 164 in FIGS. 7-10, is gravity fed from the reservoir 140 to the chamber 24 through an outlet conduit 166 (FIGS. 3 and 7-10) which carries the water 164 to a solenoid controlled manifold 168. A first normally closed fill solenoid valve 170 may be opened to direct water 164 from the conduit 166 into conduit 172 (FIGS. 7-10) which enters the chamber 24 at a lower portion thereof, such that the chamber 24 may be partially filled with water 164 from the reservoir 140 as shown in FIG. 7.

Figure 10:
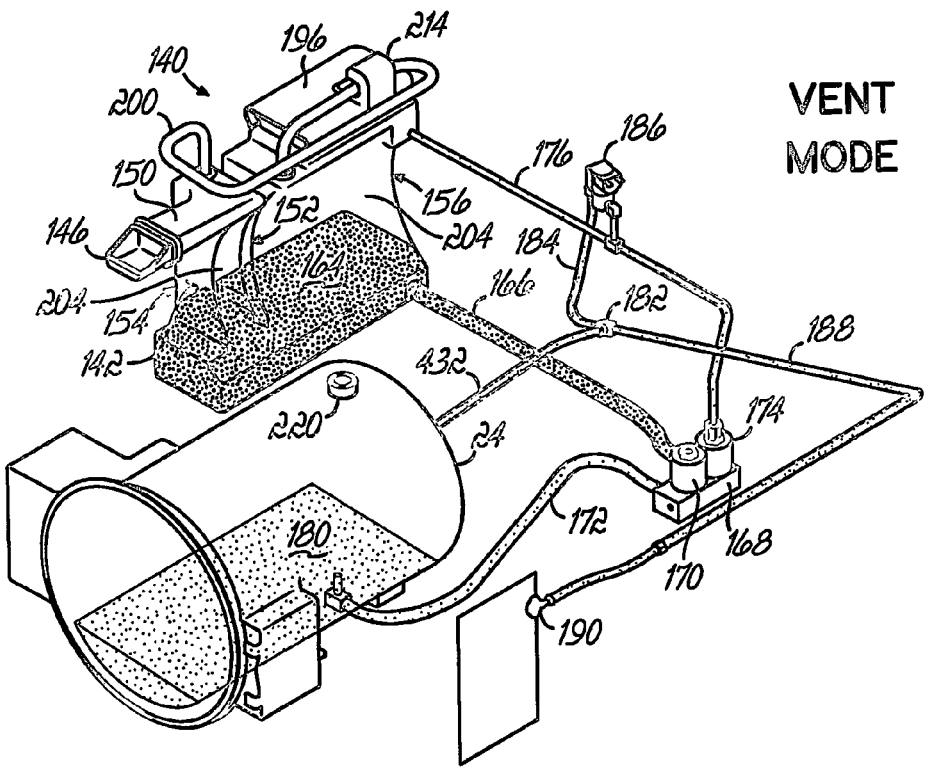

The manifold 168 further includes a second normally closed vent solenoid valve 174 which may be actuated to connect the conduit 172 to a steam conduit 176 connected to the inlet of the coil 158. Thus, with the vent solenoid valve 174 closed and fill solenoid valve 170 open, water 164 may be transferred from the reservoir 140 to the chamber 24 (FIG. 7) and, with fill solenoid valve 170 closed and vent solenoid valve 174 open, a mixture of steam and water, identified by numeral 180 in FIG. 10, may be vented back from the chamber 24 to the reservoir 140 where it is condensed by the condensing coil 158 positioned within the condensing chamber 156 (FIG. 10).

A tubular heating coil (not shown) is located in a lower portion of the chamber 24 and is supplied with power to heat the chamber 24 during a sterilization cycle. As the chamber 24 is heated by the heating coil (not shown), water 164 located within the lower portion of the chamber 24 will be evaporated to form steam and thereby facilitate transfer of heat to the articles located within the chamber 24 to be sterilized. An outlet 182 is positioned in a lower portion of the rear wall of the chamber 24 such that, as steam is formed and rises to the top portion of the chamber 24, any air in the chamber 24 will be displaced downwardly and exit through the outlet 182. The air will pass from the outlet 182 to an outlet conduit 184 having one end fluidly connected to the steam conduit 176 through an electronic air valve 186. In this way, the outlet conduit 184 is fluidly connected to the condensing coil 158 located within the condensing chamber 156 when the electronic air valve 186 is opened as will be further described in detail below.

A conduit 188 has one end fluidly connected to the outlet 182 of the chamber 24 and an opposite end fluidly connected to a pressure sensor 190, such as a pressure transducer, mounted on the control 138 as shown in FIGS. 3, 4 and 7-10. The fluid path defined by the conduit 188 from the outlet 182 to the pressure sensor 190 is always open to that the pressure sensor 190 is operable to monitor pressure within the chamber 24 at all times during the sterilization cycle as will be further described in detail below.

Figure 17:
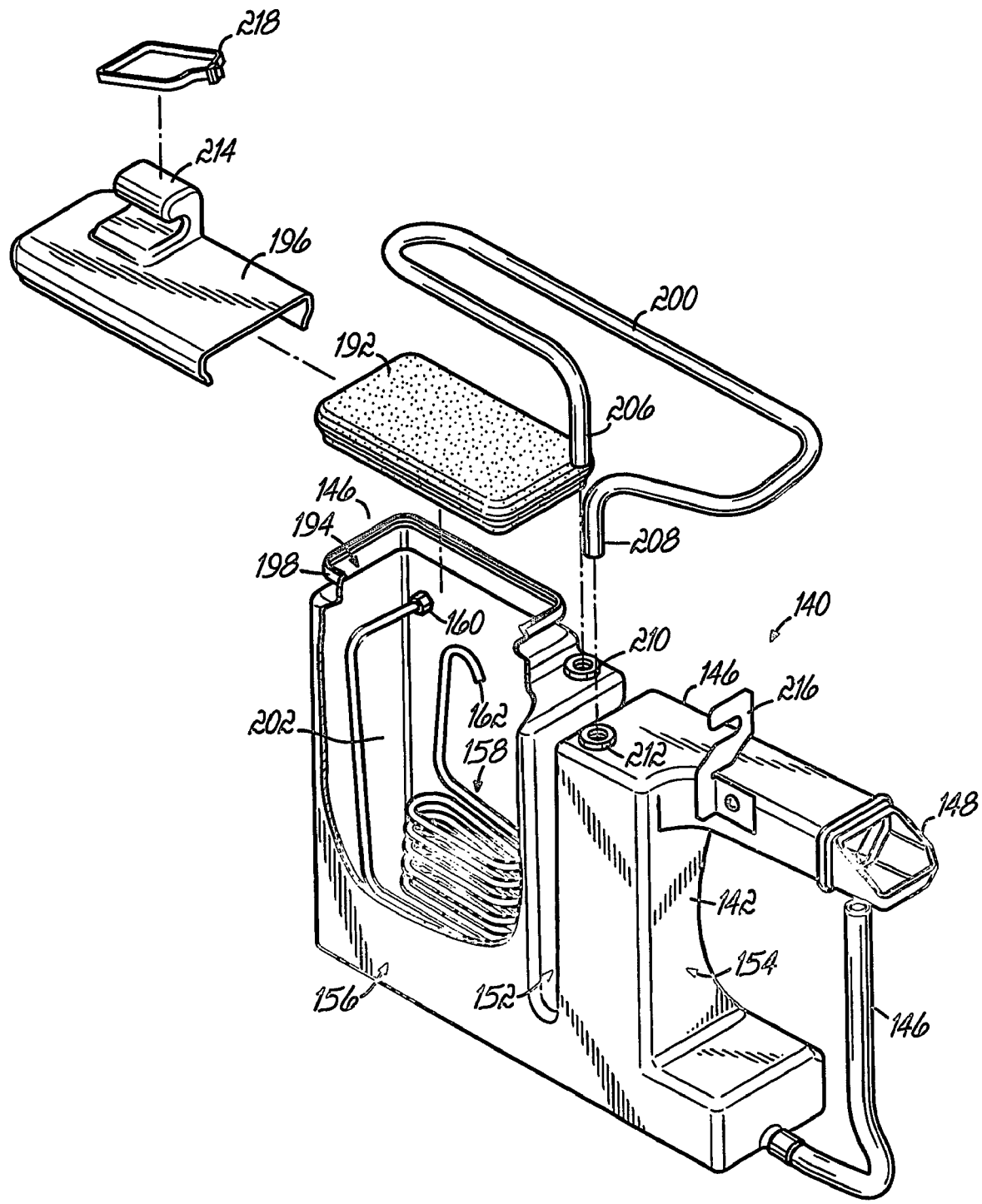
FIG. 17 is an exploded perspective view of a water reservoir used in the sterilizer.

As shown in FIG. 17, the water reservoir 140 is provided with a reservoir lid seal 192 which is attached in sealing engagement with an opening 194 formed in the upper wall 150 of the condensing chamber 156 to prevent any steam located within the upper portion of the condensing chamber 156 from exiting. A reservoir lid 196 is configured to fit over the lid seal 192 and releasably engage with a lip 198 formed about the opening 194 to retain the lid seal 192 in sealing engagement with the opening 194.

In accordance with another aspect of the present invention as shown in FIGS. 2, 3, 7-10 and 17, a steam condensing coil 200, made of copper in one embodiment, is provided to fluidly connect air spaces 202, 204 (FIGS. 7-10) of the condensing chamber 156 and the filling chamber 154, respectively, to effectively equalize the air pressures within the respective chambers 156, 154 and to condense steam within the coil 200 as the steam travels from the condensing chamber 156 to the filling chamber 154 during a sterilization cycle. Air vapors within the steam condensation coil 200 are directed to the filling chamber 154 where the air vapors may be vented to atmosphere through the fill spout 148 which is located outside of the sterilizer enclosure.

The steam condensing coil 200 has downwardly turned legs 206, 208 which extend through respective openings 210, 212 formed in the upper wall 150 of the condensing chamber 156 and the filling chamber 154. The steam condensing coil 200 is supported by a clip 214 integrally formed with the reservoir lid 196 and an upwardly extending clip 216 mounted near a front portion of the water reservoir 140. A wire tie 218 is provided to secure the coil 200 to the clip 214. The steam condensing coil 200 is supported in such a way that any condensed steam within the coil 200 will travel to the condensing chamber 156. In accordance with the principles of the present invention, the steam condensing coil 200 prevents the occurrence of excessive pressure build-up within the condensing chamber 156 as steam is vented to the condensing chamber 156 through the steam conduit 176 during the sterilization cycle.

Further, to prevent an excessive pressure build-up from occurring within the chamber 24, a pressure relief valve 220 is provided in fluid communication with the chamber 24 as shown in FIG. 3. In the event the pressure within the chamber 24 should exceed 275.8 kPa, for example, the pressure relief valve 220 opens and vents steam below the base of the sterilizer 20.

Figure 11:
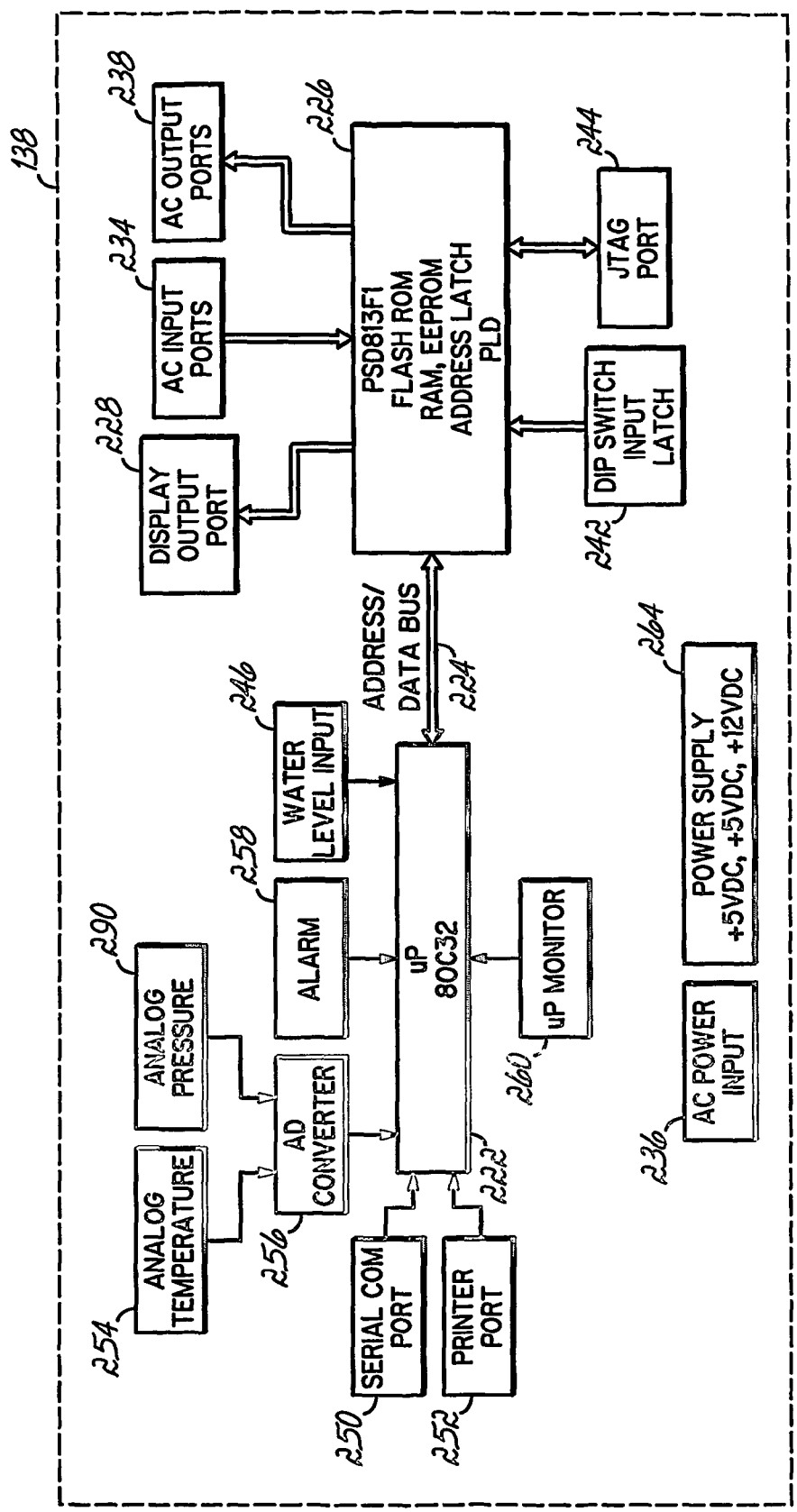
FIG. 11 is a schematic of the electrical components used in the sterilizer to control a sterilization cycle.

Circuitry of the control 138 for controlling the sterilizer 20 is shown diagrammatically in FIG. 11 and includes, in one embodiment, a microprocessor 222 which is electrically coupled through an Address/Data Bus 224 to a programmable system and multiple memory device 226. In one embodiment, the device 222 may be an 80C32 microprocessor and the device 226 may be a PSD813F1 programmable system and multiple memory device, both commercially available from ST Microelectronics of La Jolla, Calif. The device 226 includes internal Flash ROM, RAM, EEPROM, and Address Latch circuitry for storing and performing program functions and interface functions required by the sterilizer 20 during a sterilization cycle. The device 226 has a display output port 228 which is electrically coupled to an LCD display 230 (FIG. 1A) associated with a user interface 232 provided on a front portion of the sterilizer 20 so that proper operation and diagnostic information is displayed on the LCD display 230 to a user of the sterilizer 20 during a sterilization cycle as will be further described in detail below.

The device 226 has AC input ports 234 which are electrically coupled to a source 236 of AC power, and AC output ports 238 which are electrically coupled to the door relay 130, the fill solenoid valve 170, the vent solenoid valve 174, the electronic air valve 186, the heater (not shown) located within the chamber 24 and a thermostatically controlled fan 240 (FIGS. 2 and 3) located within the housing 22 of the sterilizer 20. A Dip Switch input Latch 242 is electrically coupled to the device 226 and is used to configure the program functions performed by the sterilizer 20, including service diagnostics and various display options which can be accessed by changing the dip switch positions. The device 226 includes a JTAG port 244 which permits the device 226 to communicate to external devices which are compatible with the JTAG communication protocol for programming the software of the control 138, such as through Flash programming of the device.

The microprocessor 222 has a water level input port 246 which is electrically coupled to a water level sensor 248 (FIG. 3) mounted at a lower rear end of the chamber 24. The water level sensor 248 applies an electrical signal to the microprocessor 222 when a sufficient volume of water 164 has been fed to the chamber 24 from the water reservoir 140 before a sterilization cycle is commenced. The microprocessor 222 has a serial communication port 250 which communicates with external devices which are compatible with the RS-232 serial communication protocol. The serial communication port 250 provides a bi-directional data link to the control 138 such that a remote device, such as a personal computer (PC) or other data acquisition and data generation device is able to receive sterilization cycle data and other data, including service diagnostic data, from the control 138. The serial communication port 250 also permits a remote device, such as a PC, to set parameters of the sterilization cycle and to control operation of the sterilizer 20 remotely through the PC. A printer port 252 is provided which permits the microprocessor 222 to communicate with external devices (not shown), such as to a printer (not shown) as may be desired for printing a record of a sterilization cycle.

A temperature sensor 254 (FIG. 3) is mounted at the rear end of the chamber 24 and is operable to apply an analog temperature signal to an A/D converter 256 which is electrically coupled to the microprocessor 222 so that the microprocessor 222 can monitor the temperature within the chamber 24 during a sterilization cycle. The pressure sensor 190 is electrically coupled to the microprocessor 222 and is operable to apply an analog pressure to the A/D convertor 256 so that the microprocessor 222 can monitor the pressure within the chamber 24 during a sterilization cycle. The microprocessor 222 is electrically coupled to alarms 258 that alert a user when a malfunction or improper condition of the sterilizer 20 has occurred and also to alert the user at certain predetermined stages of each sterilization cycle. A microprocessor monitor 260 is electrically coupled to the microprocessor 222 to monitor the proper function of the microprocessor 222 during a sterilization cycle and to initiate an alarm when the microprocessor 222 needs to be reset.

A normally open (NO) door interlock switch (not shown) is electrically coupled to the microprocessor 222 and applies a signal to the microprocessor 222 to indicate when the door 32 of the sterilizer 20 is closed. The water level sensor 248 and the door interlock switch (not shown) are essentially on/off switches which apply a signal to the microprocessor 222 when the water 164 within the chamber 24 reaches the height of the water level sensor 248 and when the door 32 is closed, respectively, and each of the temperature and pressure sensors 254, 190 provides a variable output which is directly proportional to the temperature and pressure within the chamber 24. Conventional 5V and 12V power supplies 264 are mounted within the sterilizer housing 22 to provide power to the control 138 and to other devices associated therewith.

The control 138 is located on a main circuit board 266 (FIGS. 2 and 4) located within the sterilizer 20 and receives manually input signals from the user interface 232 located on the front of the sterilizer 20. The user interface 232 is provided with a set of buttons or contact switches 268 through 288 for starting and stopping a sterilization cycle, for selecting a particular preprogrammed sterilization cycle, and for programming and selecting two (2) user programmable sterilization cycles as will be described in further detail below.

In one embodiment of the present invention, the user may select from four different pre-programmed cycles which are to be regulated by the control 138. These pre-programmed cycles include an "Unwrapped Cycle" for processing unwrapped articles which may be positioned directly within the sterilizer trays 30, a "Pouches" cycle for processing articles sealed within a wrapped package, a "Packs" cycle for processing articles which are grouped in a pack such as a tray containing the articles wrapped in a sealed manner by a cloth covering, for example, and a "Dental Handpiece" cycle for processing dental instruments. The cycles differ from each other with regard to the temperature to which the sterilizer chamber 24 is heated and the amount of time the sterilizer 20 remains at an elevated temperature during the sterilization portion of the sterilization cycle.

Figure 18:
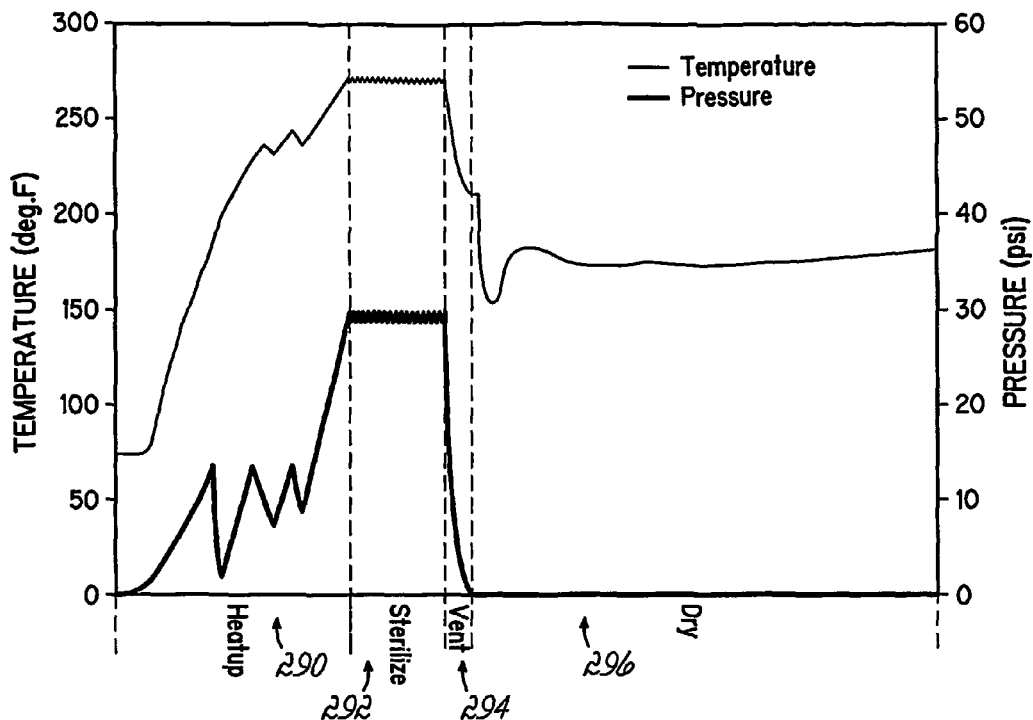
FIG. 18 is a graph illustrating process steps occurring during an exemplary sterilization cycle.

An exemplary "Unwrapped Cycle" is shown in FIG. 18 as including a "Heatup" portion 290 in which the water within the sterilizer chamber 24 is evaporated into steam to heat and pressurize the chamber 24 to a predetermined sterilization temperature and a predetermined sterilization pressure, a "Sterilize" portion 292 in which the articles within the chamber 24 are sterilized at the predetermined sterilization temperature and sterilization pressure, a "Vent" portion 294 in which the steam within the chamber 24 is vented to the water reservoir 140, and a "Dry" portion 296 in which the door 32 is automatically partially opened as illustrated in FIG. 5B after the pressure within the chamber 24 has been reduced to a level near atmospheric pressure and the heater (not shown) is operated such that any moisture remaining on the articles is caused to evaporate.

For each of the four pre-programmed cycles, the dry cycle duration of the sterilization cycle is preprogrammed for 30 minutes. However, in accordance with another aspect of the present invention, the dry cycle duration for each of the pre-programmed cycles is programmable by the user to define a user selected dry cycle duration in the range of 0-60 minutes as will further described in detail below.

In accordance with yet another aspect of the present invention, the sterilizer 20 provides the ability for a user to program two independently programmable sterilization cycles which are each stored and performed by the control 138 when the user recalls one or the other of the programmed sterilization cycles through manual actuation of either the "1" or "2" switches 270, 272 located on the user interface 232 as will be described in great detail below.

In accordance with still yet another aspect of the present invention, the sterilizer 20 has user selectable vent rates for each of the user programmable sterilization cycles which define the rate at which the sterilizer 20 vents following the "Sterilize" portion 292 of the sterilization cycle. One selectable vent rate, referred to as a "Fast Vent", causes the electronic air valve 186 to open and remain open while the steam from the chamber 24 is vented to the condensation chamber 156 of the water reservoir 140. Each of the four pre-programmed sterilization cycles is programmed with a "Fast Vent" vent rate. The other selectable vent rate, referred to as a "Slow Vent", causes the electronic air valve 186 to open for one (1) second and close for fifty-nine (59) seconds during every minute of vent time. The "Slow Vent" vent rate may be desirable when there is a need to hold the pressure within the chamber 24 and to gradually reduce the pressure so as to avoid a detrimental effect to the articles placed within the chamber 24.

In one embodiment of the present invention, the four pre-programmed sterilization cycles and the two programmable sterilization cycles have the following settings and capabilities, although other settings and capabilities are possible as well without departing from the spirit and scope of the present invention:

|  | Sterilize Temperature | Sterilize Time | Dry Cycle Time | Vent Rate |
| --- | --- | --- | --- | --- |
| Unwrapped Cycle | 270° F. | 3 minutes | Preset at 30 minutes (User Programmable 0-60 minutes) | Fast |
| Pouches Cycle | 270° F. | 5 minutes | Preset at 30 minutes (User Programmable 0-60 minutes) | Fast |
| Packs Cycle | 250° F. | 30 minutes | Preset at 30 minutes (User Programmable 0-60 minutes) | Fast |
| Dental Handpiece Cycle | 270° F. | 6 minutes | Preset at 30 minutes (User Programmable 0-60 minutes) | Fast |
| Programmable Cycle | User Programmable 230° F.-275° F. | User Programmable 3-90 minutes | User Programmable 0-60 minutes | User Programmable Fast or Slow |

Referring now to the flow charts shown in FIGS. 12-16, and with reference to the diagrammatic views of the components of the sterilizer 20 as shown in FIGS. 7-10, the operation of the sterilizer 20 during an exemplary sterilization cycle for sterilizing articles within the chamber 24 will now be described.

Figure 12:
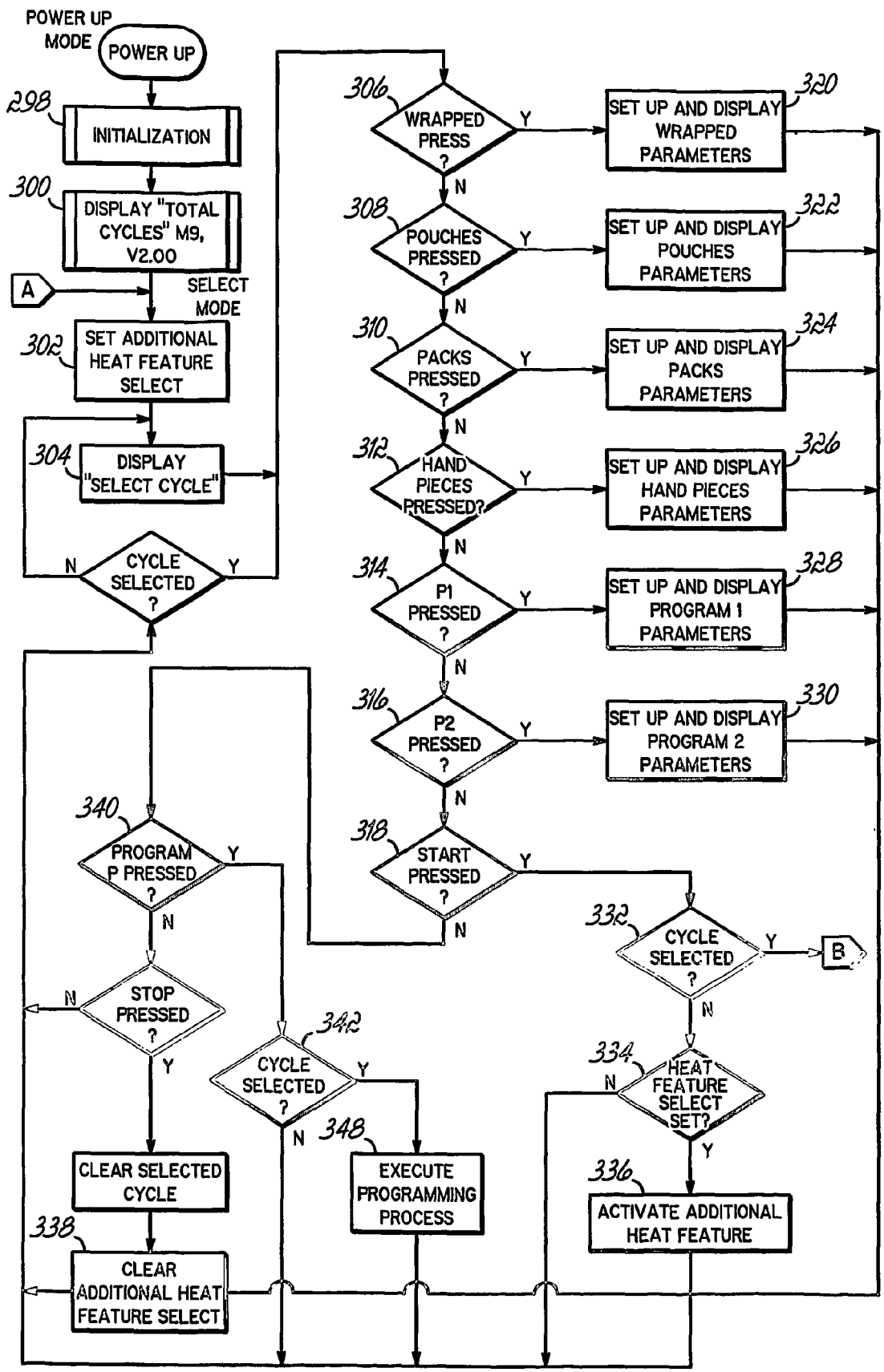
FIGS. 12-16 are flow charts depicting the operation of the sterilizer during a sterilization cycle.

Referring to FIG. 12, the "Power Up Mode" and "Select Mode" routines will be described in connection with power up of the sterilizer 20 and selection of one of the four pre-programmed or two programmed sterilization cycles by the user. Initially, after articles to be sterilized have been placed within the chamber 24 and the user has turned the sterilizer on, the control 138 executes the "Power Up Mode" to perform a system initialization of the sterilizer 20 at block 298 and thereafter displays text information regarding the "Total Cycles" performed by the sterilizer 20 on the LCD display 230 at block 300.

Figure 1A:
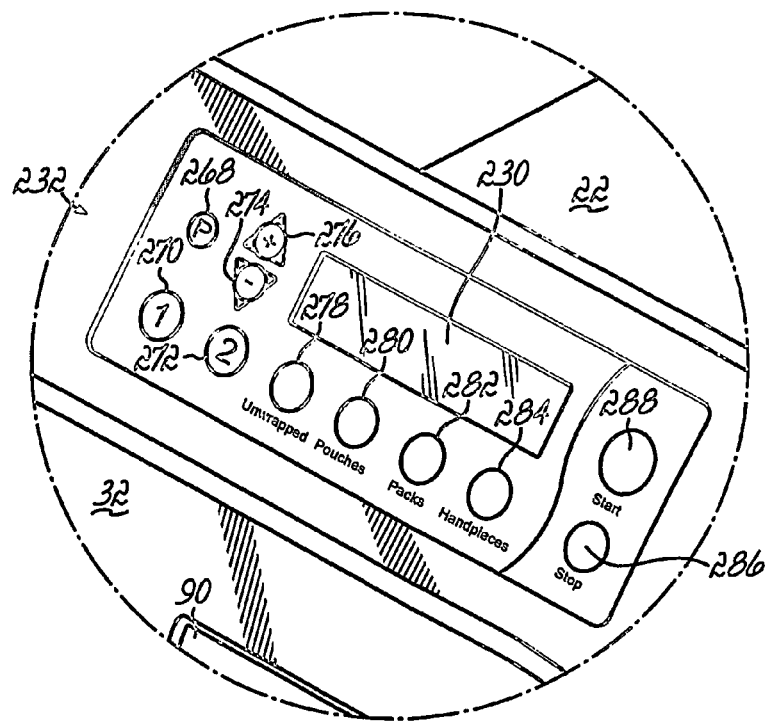
FIG. 1A is an enlarged view of the circled area in FIG. 1, illustrating a user interface of the sterilizer.

After execution of the "Power Up Mode" routine, the control 138 executes the "Select Mode" routine to determine which, if any, of the switches 268 through 288 of the user interface 232 have been depressed by the user. As shown in FIG. 1A, these switches comprise the "Start" switch 288, the "Stop" switch 286, the four pre-programmed sterilization cycle switches 278 through 284 corresponding to the "Unwrapped", "Pouches", "Packs" and "Handpieces" sterilization cycles, the program "P" switch 268 which permits programming of the two programmable sterilization cycles, and the "1" and "2" switches 270 and 272 which are used in the programming process of the two programmable sterilization cycles as well as recalling the programmed parameters of the two programmable sterilization cycles, and the "+" and "−" switches 274 and 276 which permit a user to increment or decrement certain parameters during programming of the sterilization cycles.

Further referring to the "Select Mode" routine of FIG. 12, the control 138 sets at block 302 the "Additional Heat Feature". This feature is used to operate the heater (not shown) for ten (10) minutes to pre-warm the sterilizer 20 before use or to provide additional heating to articles within the chamber 24 following the dry cycle portion 296 of the sterilization cycle. After the "Additional Heat Feature" has been set at block 302, the control 138 displays the text "Select Cycle" on the LCD display 230 at block 304 to notify the user that the sterilizer 20 is prepared to receive a sterilization cycle selection from the user.

During execution of the "Select Mode" routine, the control 138 checks at blocks 306 through 318 whether any of the four pre-programmed sterilization cycle switches 278 through 284, the two programmable sterilization cycle switches 270, 272, or the "Start" switch 288 has been depressed by the user. In the event the user has depressed one of the pre-programmed or programmable sterilization cycle switches 270, 272 and 278 through 284, the control 138 sets up the sterilizer 20 with the parameters for the selected sterilization cycle as described in the chart above and displays the parameters for the selected sterilization cycle on the LCD display 230 at blocks 320 through 330.

At block 318, the control 138 checks whether the "Start" switch 288 has been depressed and at block 332 whether a sterilization cycle has been selected by the user. If yes, the control 138 proceeds to execute the "Fill Mode" and "Heat Up Routines" routines as will be described in detail below in connection with FIG. 13.

In the event the "Start" switch 288 has been depressed as determined at block 318 but none of the sterilization cycle switches 270, 272 and 278 through 284 has been depressed as determined at block 332, the control 138 checks whether the "Additional Heat Feature" has been set at block 334. If yes, the "Additional Heat Feature" is activated at block 336 to operate the heater (not shown) for 10 minutes to heat the sterilization chamber 24. The "Additional Heat Feature" will be deactivated within the 10 minute duration if any one of the pre-programmed or programmable sterilization cycle switches 270, 272 and 278 through 284 is depressed as indicated at block 338.

In the event none of the preprogrammed or programmable sterilization cycle switches 270, 272 and 278 through 284 is depressed and the "Start" switch 288 is not depressed as well, the control 138 checks at block 340 whether the program "P" switch 268 has been depressed and at block 342 whether either of the "1" or "2" programmable cycle switches 270, 272 has been pressed. If the "P" switch 268 has not been depressed, the control 138 checks at block 344 whether the "Stop" switch 286 has been pressed. If yes, the control 138 clears the selected sterilization cycle at block 346 and clears the "Additional Heat Feature" at block 338.

In the event the program "P" switch 268 is depressed and one of the programmable cycle "1" or "2" switches 270, 272 is depressed as determined at blocks 340 and 342, the control 138 proceeds to execute a programming process for the selected programmable cycle "1" or "2" at block 348. Each of the programmable cycles is programmed by the user first depressing the program "P" switch 268 followed by the user depressing either the cycle "1" or "2" switches 270, 272. When this has occurred, the control 138 displays the Program Number "1" or "2" on the LCD display 230 and also the presently programmed sterilization temperature, sterilization time, dry cycle time and vent rate for that programmed cycle. The control 138 then displays the presently programmed sterilization temperature on the LCD display 230 so that the user can raise or lower the programmed sterilization temperature by depressing the "+" or "−" switches 276, 274 to increment or decrement the sterilization temperature in one degree increments until the desired sterilization temperature is selected between a range of 230° F. and 275° F.

The user is then prompted on the LCD display 230 to depress either the program "P" switch 268 to continue the programming process for the selected cycle or the "Stop" switch 286 to terminate the programming process. In the event the user depresses the program "P" switch 268, the control 138 displays the presently programmed sterilization time in minutes on the LCD display 230 and the user can increment or decrement the sterilization time in one minute increments using the "+" or "−" switches 276, 274 until the desired sterilization time is selected between a range of 3 and 90 minutes.

This same process continues to allow the user to program vent type (i.e., "Fast" or "Slow") and the dry time in a range between 0 and 60 minutes in one minute increments. After the programming process is completed, the control 138 displays the new programmed parameters for the selected programmable sterilization cycle on the LCD display 230 and these parameters are stored by the control 138.

Figure 13:
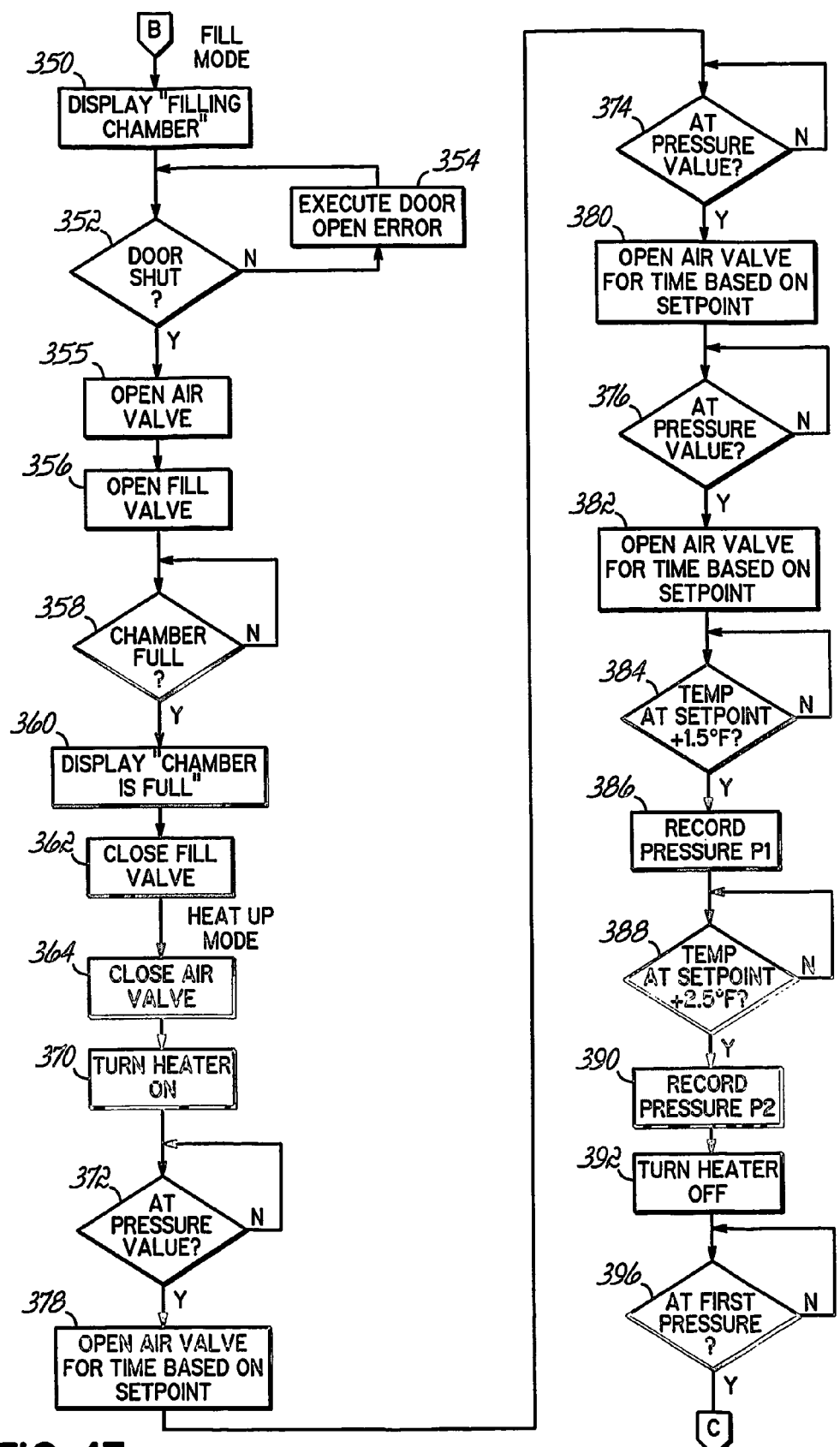

Referring now to FIG. 13, the "Fill Mode" and "Heat Up Mode" routines will now be described. In the even the "Start" switch 288 has been depressed and one of the preprogrammed or programmable sterilization cycles has been selected as determined at blocks 318 and 332 of FIG. 12, the control 138 displays the text "Filling Chamber" on the LCD display 230 at block 350. The control 138 checks at block 352 whether the door 32 is closed by checking the status of the door interlock switch (not shown). If the door 32 is not closed, the control 138 executes a "Door Open Error" routine at block 354. If the door 32 is closed, the control 138 proceeds to open the electronic air valve 186 at block 355 and the fill solenoid valve 170 at block 356 so that water, indicated by numeral 164 in FIG. 7 which illustrates the "Fill Mode", is gravity fed from the water reservoir 140 to the sterilization chamber 24. The control 138 checks at block 358 whether the chamber 24 is sufficiently full with water 164 through the water level sensor 248. When the chamber 24 is sufficiently full with water 164, the control 138 displays the text "Chamber is Full" on the LCD display 230 at block 360 and then closes the fill solenoid valve 170 at block 362.

Figure 8:
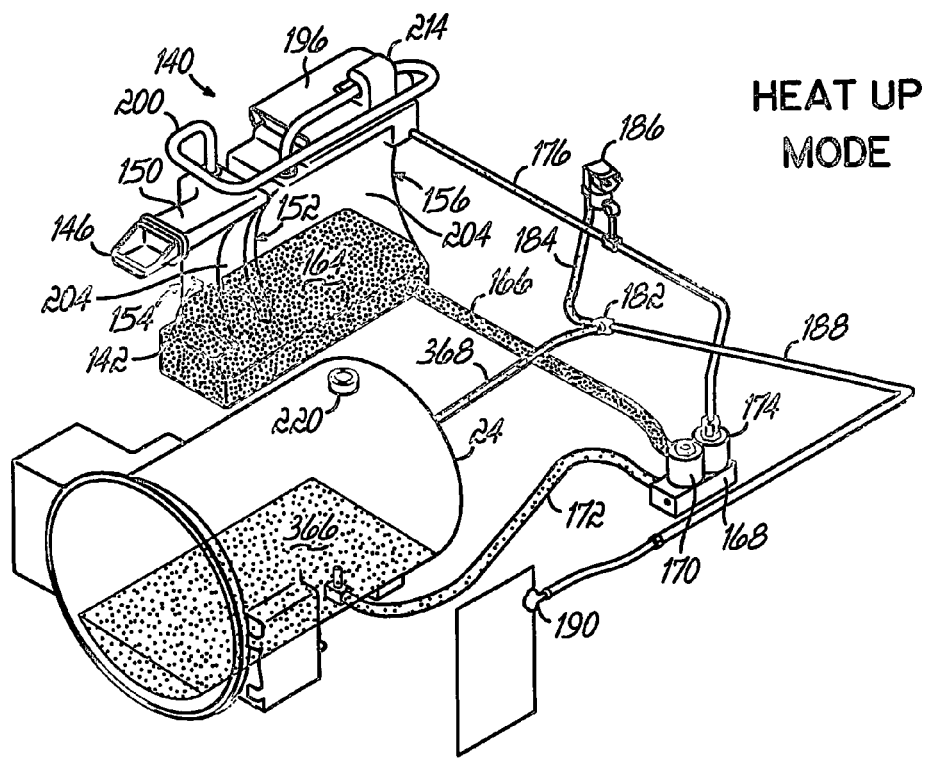

Still referring to FIG. 13, the control 138 then proceeds to the "Heat Up Mode" routine. During execution of the "Heat Up Mode" routine, control 138 closes the electronic air valve 186 at block 364 and operates the heater (not shown) to start heating and evaporating the water within the chamber 24 into steam to heat and pressurize the sterilization chamber 24. FIG. 8 illustrates the "Heat Up Mode" and the heated water is indicated by numeral 366 and a mixture of air and steam is indicated by numeral 368.

In accordance with another aspect of the present invention, as illustrated diagrammatically in FIG. 18, the control 138 is operable to open and close the electronic air valve 186 multiple times, i.e., three (3) times in one embodiment, as the sensed steam temperature rises toward the sterilization temperature set point. In particular, the control 138 opens the electronic air valve 186 to vent the mixture 368 of air and steam from the chamber 24 to the water reservoir 140 multiple times during the "Heat Up Mode" so that residual air within the chamber 24 is vented to obtain an optimum saturated environment of steam within the chamber 24 during the sterilization cycle. In one embodiment, the control 138 opens the electronic air valve 186 during three (3) equal intervals during the "Heat Up Mode" when the sensed chamber pressure is about one half of the chamber pressure set point for the selected sterilization temperature set point as shown in FIG. 18. The control 138 opens the electronic air valve 186 three (3) times during the "Heat Up Mode" for a specific amount of time based on Bernoulli's equation to reduce the amount of air retained in the sterilization chamber 24 as the chamber temperature rises toward the sterilization temperature set point.

Referring again to the "Heat Up Mode" routine of FIG. 13, after the heater is turned on at block 370, the control 138 checks the chamber pressure at blocks 372, 374 and 376 to determine whether the sensed chamber pressure is approximately one half of the chamber pressure set point for the selected sterilization temperature set point as described in detail above. In the event the sensed chamber pressure is approximately one half of the chamber pressure set point for the selected sterilization temperature set point, the control 138 opens the electronic air valve 186 at blocks 378, 380 and 382 to vent the mixture 368 of air and steam to the water reservoir 140 so that an optimum saturated environment of steam can be obtained in the sterilization chamber 24.

Figure 19:
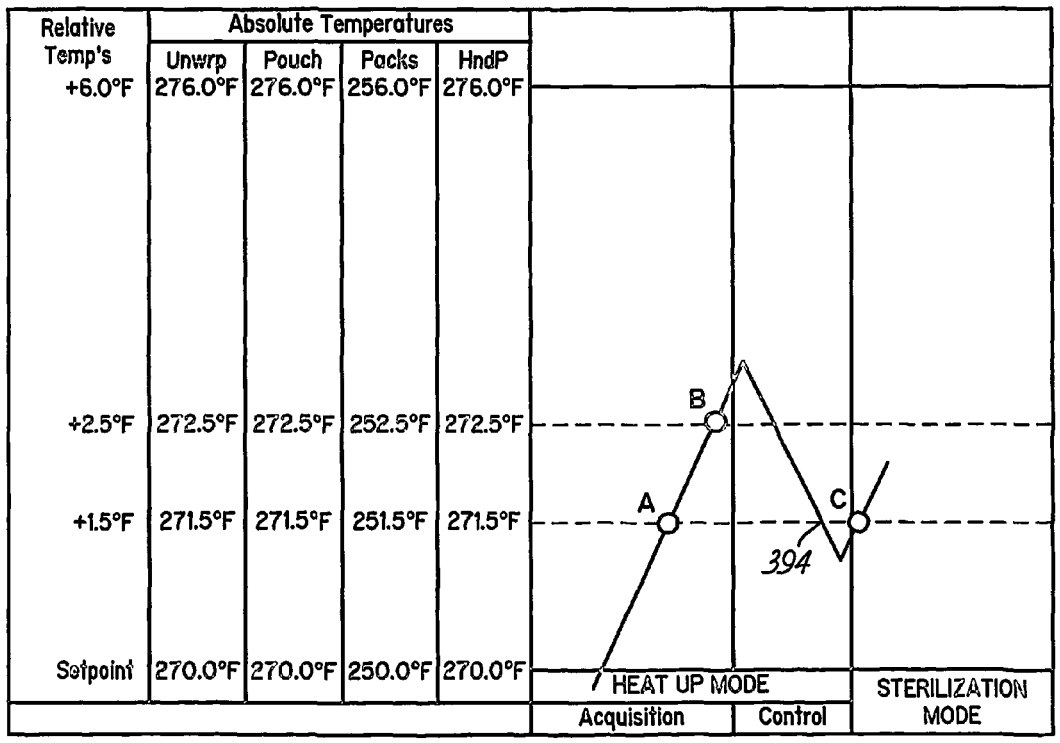
FIG. 19 is a graph illustrating process steps occurring during a portion of an exemplary sterilization cycle.

In accordance with yet another aspect of the present invention, as shown in FIG. 19, the sterilizer 20 of the present invention utilizes chamber pressure to control operation of the heater (not shown) as the heater heats the chamber 24 to the sterilization temperature set point. Further referring to FIGS. 13 and 19, under normal conditions, steam temperature within the chamber rises continually until it reaches a point "A" (FIG. 19) that is 1.5° F. above the sterilization temperature set point of the selected sterilization cycle. Once the steam temperature within the chamber 24 reaches point "A" as determined by the sensed chamber temperature at block 384, control 138 records the sensed chamber pressure at point "A" at block 386. This may be referred to as the "On Pressure". The heater continues to be energized and the steam temperature within the chamber 24 continues to rise. When the sensed chamber temperature reaches 2.5° F. above the sterilization temperature set point as determined by the sensed chamber temperature at block 388, the control 138 records the sensed chamber pressure at point "B" at block 390 and the heater (not shown) is turned off at block 392. This may be referred to as the "Off Pressure". The chamber temperature drops until the sensed chamber pressure reaches the "On Pressure" at point 394 as determined at block 396. Once the "On Pressure" is sensed at point 394, the heater (not shown) is again energized at block 398 of FIG. 14 to heat the chamber 24. When the sensed chamber pressure reaches the "On Pressure" at point "C" the control 138 proceeds to execute the "Sterilize Mode" illustrated in FIG. 14.

Figure 9:
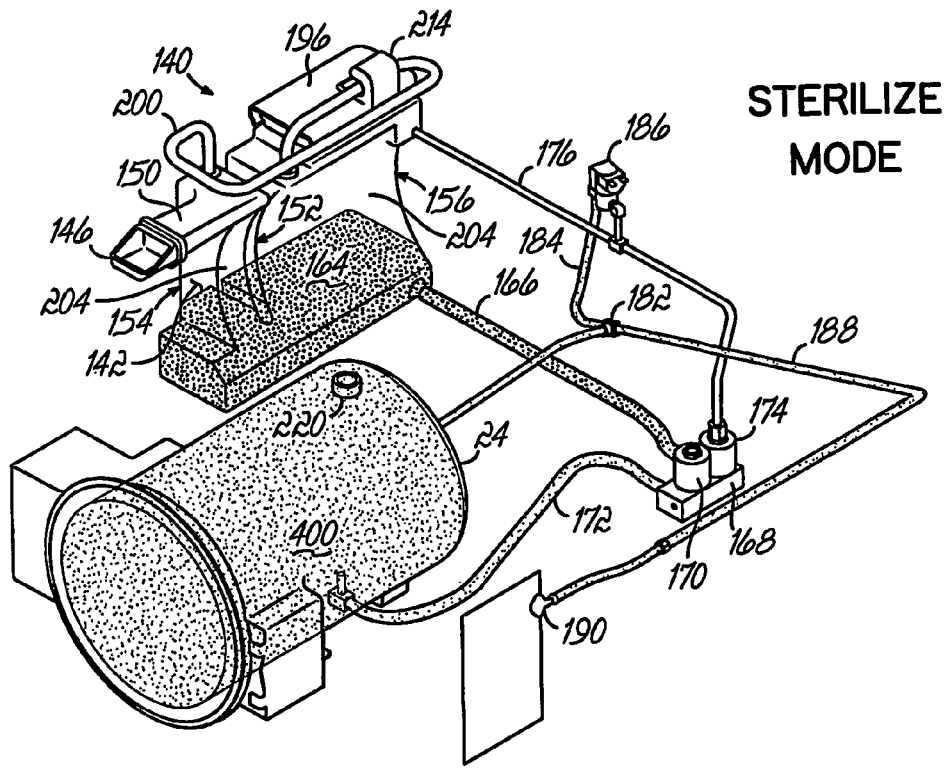
Figure 14:
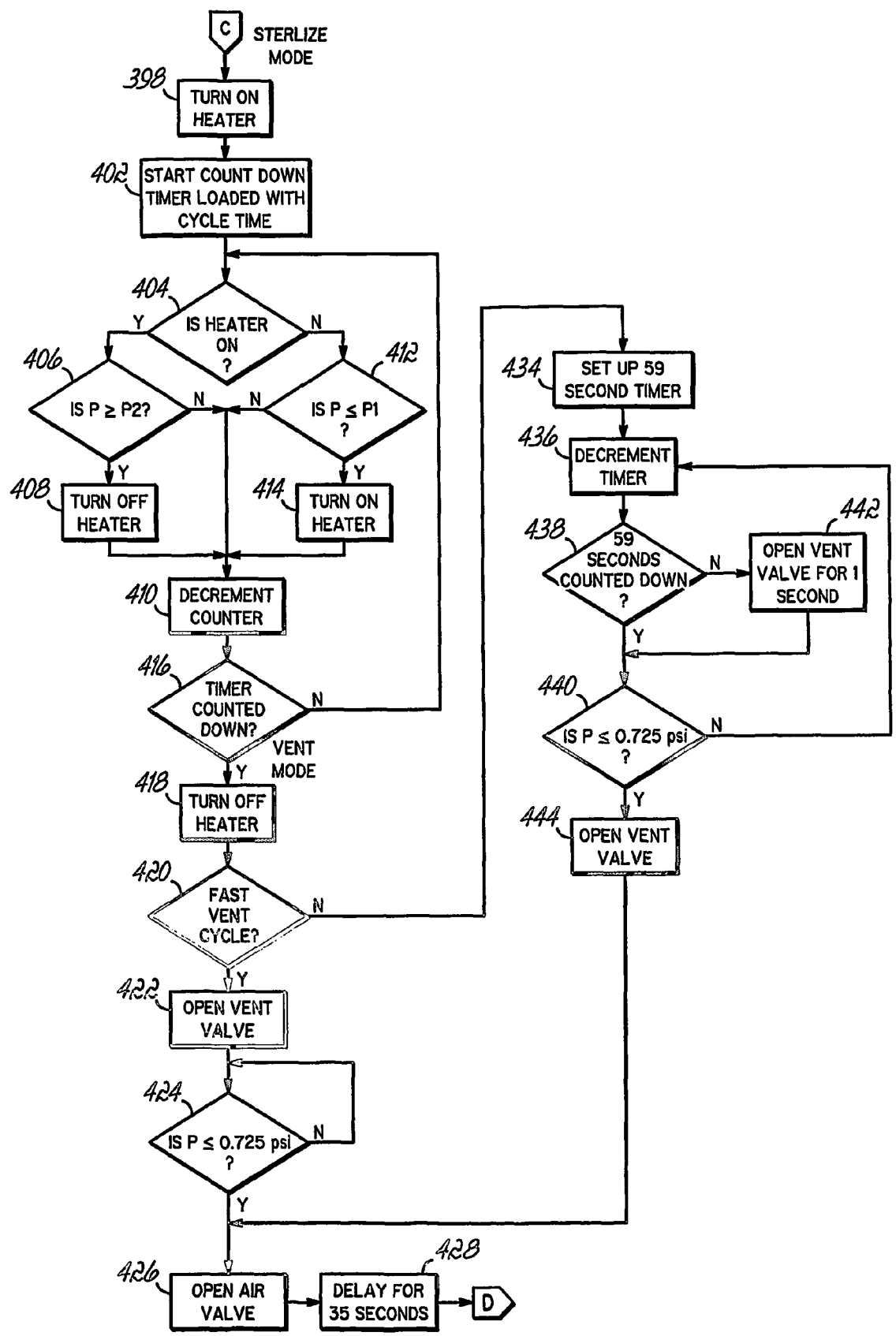

Referring now to FIGS. 9 and 14, the "Sterilize Mode" will now be described. Once in "Sterilize Mode", the chamber temperature is regulated so that if the sensed chamber pressure falls below the "On Pressure", the heater (not shown) is turned on. If the sensed chamber pressure rises above the "Off Pressure", the heater (not shown) is turned off, and so on until the end of the "Sterilize Mode". If the sensed chamber temperature falls below 1° F. above the selected sterilization temperature set point, the heater (not shown) is automatically turned on and the "On Pressure" and "Off Pressure" are re-acquired. Once they are reacquired, the sterilizer 20 resumes performing relative barostatic temperature control as described in detail above. In this way, the chamber temperature is accurately maintained very close to the sterilization temperature set point so that the chamber 24 sterilizes the articles placed within the chamber with a mixture of air and steam as indicated by numeral 400 in FIG. 9.

At block 402 of the "Sterilize Mode", the control 138 starts a count down timer which has been loaded with the sterilization cycle time. At block 404, the control 138 determines if the heater (not shown) is turned on. If the heater is turned on, the control 138 determines at block 406 whether the sensed chamber pressure is equal to or greater than the "Off Pressure". If the sensed chamber pressure is equal to or greater than the "Off Pressure", the heater is turned off at block 408 and the counter is decremented at block 410. Otherwise, the counter is directly decremented at block 410 from block 406.

If the heater is not turned on as determined at block 404, the control 138 makes a determination at block 412 whether the sensed chamber pressure is less than or equal to the "On Pressure". If the sensed chamber pressure is less than or equal to the "On Pressure", the heater is turned on at block 414 and the the counter is decremented at block 410. Otherwise, the counter is directly decremented at block 410 from block 412.

At block 416, the controls determines whether the timer has counted down, thereby indicating the "Sterilize Mode" is completed. If not, control passes back to block 404. Otherwise, If the "Sterilize Mode" is completed, the control 138 executes the "Vent Mode" routine illustrated in FIG. 14 and turns the heater off at block 418.

Referring now to FIGS. 10 and 14, the control 138 determines at block 420 whether the selected sterilization cycle has a "Fast" vent rate. If yes, the vent solenoid valve 174 is opened at block 422 and the control 138 determines at block 424 whether the sensed chamber pressure is less than or equal to 0.725 psi in one embodiment of the present invention. If so, the control 138 opens the electronic air valve 186 at block 426 and establishes a delay for thirty-five (35) seconds at block 428 and then the control 138 executes the "Door Open Mode" routine illustrated in FIG. 15. In this way, the mixture of steam and water, indicated by numeral 180 in FIG. 10, is vented to the water reservoir 140 through the vent solenoid valve 174 and a mixture of steam and air, indicated by numeral 432 in FIG. 10, is vented to the water reservoir 140 through the electronic air valve 186.

Further referring to FIG. 14, if the control 138 determines that the selected sterilization cycle does not have a "Fast" vent rate, the control 138 sets up a fifty-nine (59) second timer at block 434 and decrements the timer at block 436. The control 138 determines at block 438 whether the timer has counted down and if so, control 138 determines at block 440 whether the sensed chamber pressure is less than or equal to 0.725 psi. If the timer has not counted down, the control 138 opens the solenoid vent valve 174 for one (1) second at block 442 and control then passes to block 440.

If the control 138 determines at block 440 that the sensed chamber pressure is less than or equal to 0.725 psi, the solenoid vent valve 174 is opened at block 444 then passes to block 426 to open the electronic air valve 186. Otherwise, control passes to decrement the counter at block 436.

Figure 15:
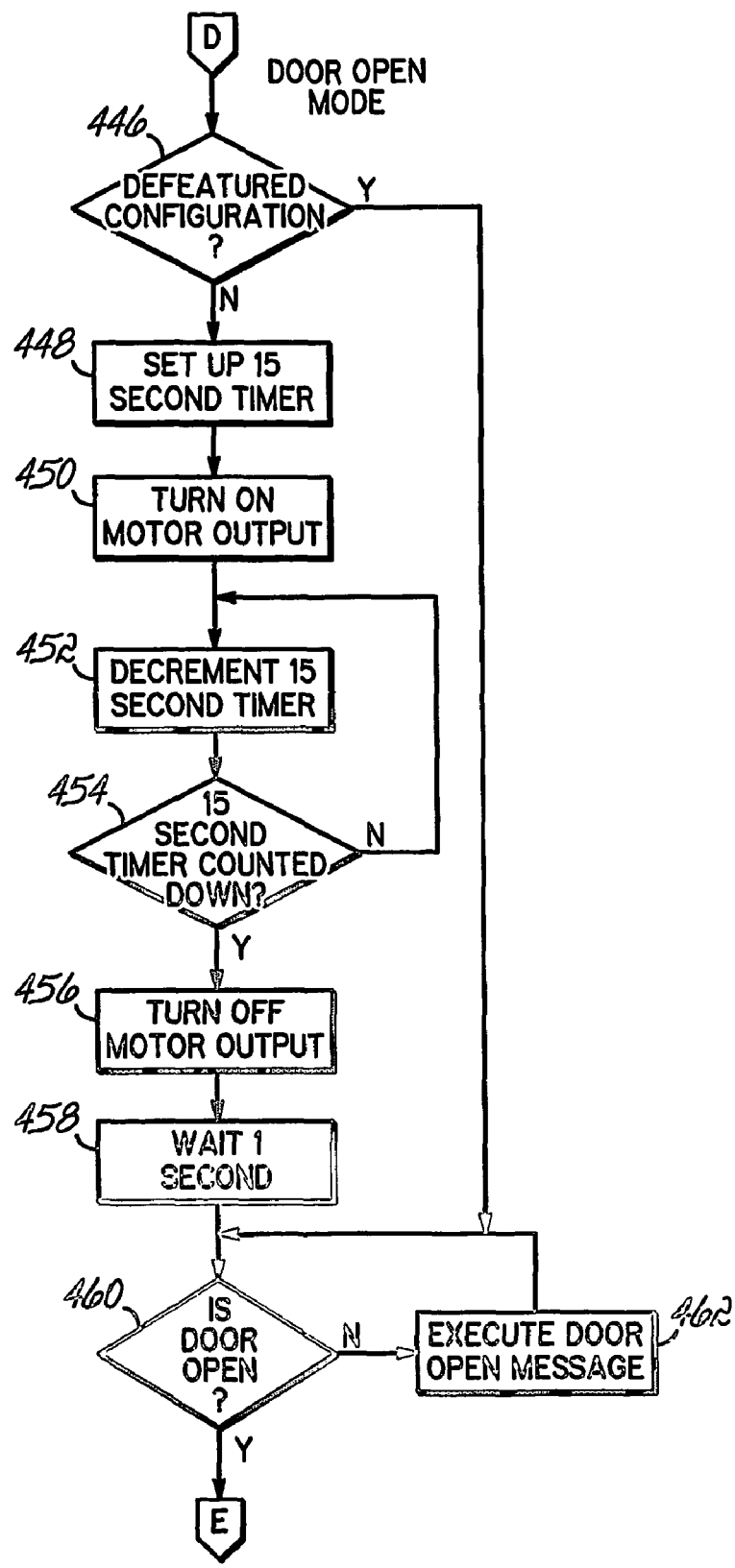

Referring now to the "Door Open Mode" routine of FIG. 15, the control 138 determines at block 446 whether the sterilizer 20 is a "defeatured" configuration which does not include an automatic door opening control. If the sterilizer 20 includes an automatic door control, the control 138 sets up a fifteen (15) second timer at block 448 and energizes the synchronous motor 114 at block 450 to initiate a release of the door lock mechanism as described in detail above in connection with FIGS. 5A, 5B and 6. The fifteen (15) second timer is decremented at block 452 and the control determines at block 454 whether the timer has counted down. If not, control returns to block 452 to decrement the timer. If the timer has counted down, the motor 114 is de-energized at block 456 and a one (1) second delay is established at block 458. At block 460, for "defeatured" sterilizers and sterilizers having an automatic door control, the control 138 determines if the door 32 is open through the door interlock switch (not shown). If the door 32 is open, the control 138 executes the "Dry Mode" routine of FIG. 16. Otherwise, the control 138 executes a "Door Open Message" on the LCD display 230 at block 462.

Figure 16:
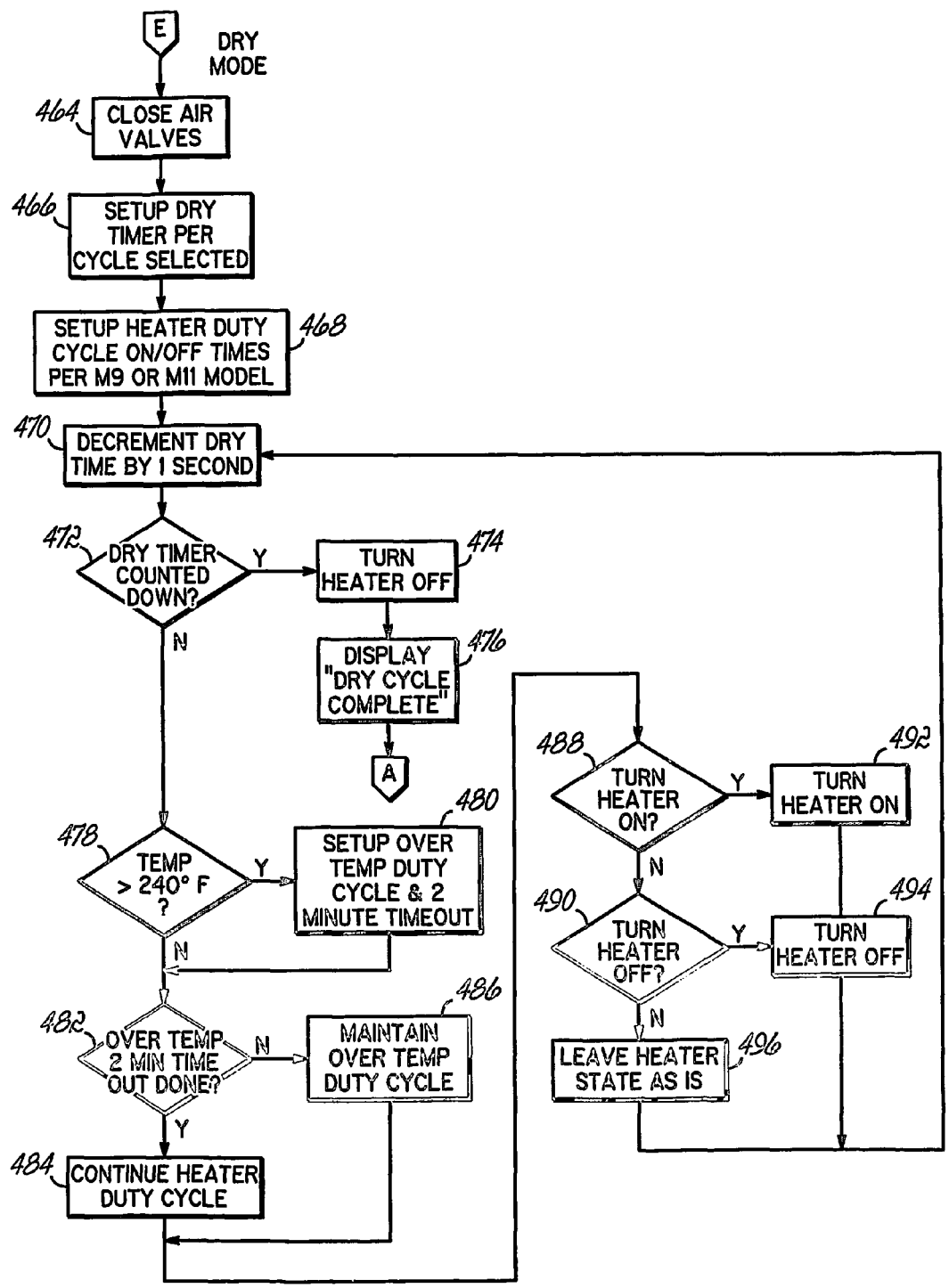

Referring now to FIG. 16, the "Dry Mode" routine executed by the control 138 is illustrated. At block 464, the control 138 closes the electronic air valve 186 and sets up a dry timer at block 466 with the dry time associated with the selected sterilization cycle. The control 138 sets up the heater duty cycle at block 468 and then decrements the dry time counter by one (1) second at block 470. The control 138 determines at block 472 whether the dry timer has counted down, and if so, the control turns off the heater at block 474 and displays the text "Dry Cycle Complete" on the LCD display 230 at block 476.

If the dry cycle timer has not counted down at block 472, the control 138 determines whether the sensed chamber temperature exceeds 240° F. at block 478. If yes, the control 138 sets up an over temperature duty cycle and a two minute timer at block 480 and control then passes to block 482 where the control 138 determines whether the timer has counted down. If the sensed chamber temperature does not exceed 240° F., control passes directly from block 478 to block 482.

If the timer has counted down, the control 138 at block 484 continues the heater duty cycle set up at block 468. Otherwise, the control 138 maintains at block 486 the over temperature duty cycle set up at block 480 and control passes to blocks 488 and 490 where the control determines whether the heater (not shown) should be turned on or off according to the particular set duty cycle and turns the heater either on or off at blocks 492 and 494 according to the set duty cycle. Otherwise, the control 138 leaves the heater in its present state at block 496 and control then passes to block 470 to decrement the dry timer by one second. The "Dry Mode" routine continues until the dry cycle is completed.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicants' general inventive concept.

Having described the invention, what is claimed is:

1. A sterilizing apparatus for sterilizing articles, comprising:
    an outer housing;
    a sterilizer chamber enclosed within said housing;
    a water reservoir in fluid communication with said chamber and operable to supply water to said chamber;
    an opening formed in said housing and said chamber configured to permit articles to be placed inside said chamber;
    a door mounted on a front portion of said housing for movement toward and away from said opening;
    a door lock mechanism comprising housing mounted components positioned within said housing adjacent said opening and door mounted components configured to engage said housing mounted components;
    a motor having a rotatable shaft, a rotatable cam, and a rod mounted within said housing, said motor being operable to rotate said cam to thereby move said rod axially to produce engagement and disengagement of said housing mounted components with said door mounted components;
    a first stop member in said housing and positioned to be contacted by said cam to thereby limit rotation thereof;
    a switch spaced from said first stop member and positioned to be contacted by said cam when said cam contacts said first stop member; and
    a second stop member positioned to be contacted by said cam to thereby limit rotation thereof, said switch being the only switch contacted by said cam during rotation thereof between the contacting positions of said cam with said first and second stop members.

2. The sterilizing apparatus of claim 1, wherein said housing mounted components include a bar dispensed transverse to said rod, said rod being coupled to said bar substantially at a longitudinal end of said bar.

3. A sterilizing apparatus for sterilizing articles, comprising:
    an outer housing;
    a sterilizer chamber enclosed within said housing;
    a water reservoir in fluid communication with said chamber and operable to supply water to said chamber;
    an opening formed in said housing and said chamber configured to permit articles to be placed inside said chamber;
    a door mounted on a front portion of said housing for movement toward and away from said opening;
    a door lock mechanism comprising housing mounted components positioned within said housing adjacent said opening and door mounted components configured to engage said housing mounted components;
    a motor having a rotatable shaft, a rotatable cam, and a rod mounted within said housing, said motor being operable to rotate said cam to thereby move said rod axially to produce engagement and disengagement of said housing mounted components with said door mounted components;
    a first stop member in said housing and positioned to be contacted by said cam to thereby limit rotation thereof;
    a switch spaced from said first stop member and positioned to be contacted by said cam when said cam contacts said first stop member; and
    a second stop member engageable by said cam to thereby limit rotation thereof, said cam being free from contacting engagement with any switches when said second stop member is engaged by said cam.

4. The sterilizing apparatus of claim 3, wherein said cam includes a first flat surface and said first stop member includes a second flat surface, contacting of said cam with said first stop member including contacting engagement of said first and second flat surfaces with one another.

5. The sterilizing apparatus of claim 4, wherein said cam includes a rounded surface, contacting of said switch by said cam including contacting of said switch by said rounded surface.

6. The sterilizing apparatus of claim 3, wherein said housing mounted components include a bar disposed transverse to said rod, said rod being coupled to said bar substantially at a longitudinal end of said bar.

7. A sterilizing apparatus for sterilizing articles, comprising:
    an outer housing;
    a sterilizer chamber enclosed within said housing;
    a water reservoir in fluid communication with said chamber and operable to supply water to said chamber;
    an opening formed in said housing and said chamber configured to permit articles to be placed inside said chamber;
    a door mounted on a front portion of said housing for movement toward and away from said opening;

a door lock mechanism comprising housing mounted components positioned within said housing adjacent said opening and door mounted components configured to engage said housing mounted components;

a motor having a rotatable shaft, a rotatable cam, and a rod mounted within said housing, said motor being operable to rotate said cam to thereby move said rod axially to produce engagement and disengagement of said housing mounted components with said door mounted components;

a first stop member in said housing and positioned to be contacted by said cam to thereby limit rotation thereof;

a switch spaced from said first stop member and positioned to be contacted by said cam when said cam contacts said first stop member; and a second stop member positioned to be contacted by said cam to thereby limit rotation thereof, each of said first and second stop members having respective stop member flat surfaces lying generally in a common plane, said cam including first and second cam flat surfaces selectively lying in said common plane when said cam respectively contacts said first and second stop members.

* * * * *

UNITED STATES PATENT AND TRADEMARK OFFICE
CERTIFICATE OF CORRECTION

| | | |
|---|---|---|
| PATENT NO. | : 7,951,342 B2 | Page 1 of 1 |
| APPLICATION NO. | : 10/556479 | |
| DATED | : May 31, 2011 | |
| INVENTOR(S) | : Gary Benning et al. | |

It is certified that error appears in the above-identified patent and that said Letters Patent is hereby corrected as shown below:

Title Page,
Item (57), Abstract, reads "valve (186) is provided to control the venting rate of the steam is vented back to a water reservoir" and should read -- valve (186) is provided to control the venting rate of the steam as the steam is vented back to a water reservoir --.

Column 2
Line 2, reads "very dose to the" and should read -- very close to the --.

Column 7
Line 18, reads "In Its rest position" and should read -- In its rest position --.

Column 8
Line 45, reads "sensor 190 is always open to that the" and should read -- sensor 190 is always open so that the --.

Column 11
Line 8, reads "including a "Heatup" portion 290" and should read -- including a "Heat Up" portion 290 --.

Column 14
Line 17, reads "In the even the" and should read -- On the event that the --.

Column 16
Line 14, reads "If the" and should read -- if the --.

Signed and Sealed this
Twenty-ninth Day of November, 2011

David J. Kappos
*Director of the United States Patent and Trademark Office*